(12) United States Patent
Kandori et al.

(10) Patent No.: US 6,275,719 B1
(45) Date of Patent: Aug. 14, 2001

(54) BIOMAGNETIC FIELD MEASUREMENT APPARATUS

(75) Inventors: Akihiko Kandori, Hachioji; Tsuyoshi Miyashita, Kokubunji; Keiji Tsukada, Kashiwa; Hitoshi Sasabuchi, Mito; Hiroyuki Suzuki, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/293,885

(22) Filed: Apr. 19, 1999

(30) Foreign Application Priority Data

Sep. 9, 1998 (JP) .................................. 10-254847

(51) Int. Cl.[7] ...................................... A61B 5/05
(52) U.S. Cl. .............................. 600/409; 324/248
(58) Field of Search .................... 600/409; 324/244, 324/248

(56) References Cited

U.S. PATENT DOCUMENTS

| | | | |
|---|---|---|---|
| 5,142,229 | * 8/1992 | Marsden | 324/248 |
| 5,285,385 | * 2/1994 | Igarashi et al. | 600/409 |
| 5,437,276 | * 8/1995 | Takada | 324/248 |
| 5,891,031 | * 4/1999 | Ohyu | 600/409 |
| 6,023,633 | * 2/2000 | Kado | 600/409 |

FOREIGN PATENT DOCUMENTS

| | | | |
|---|---|---|---|
| 19827245 | * 12/1998 | (DE) | |
| 7-297456 | 10/1995 | (JP) | |
| 8-266499 | * 10/1996 | (JP) | |
| 9402864 | * 2/1994 | (WO) | 324/248 |

OTHER PUBLICATIONS

Handbook of Clinical Engineering, 1984, pp. 474–475.
Phys. Med. Biol., vol. 32, No. 1, 1987, pp. 11–22.
Journal of Magnetism and Magnetic Materials, 22, 1981, pp. 154–157.

* cited by examiner

Primary Examiner—John A. Jeffery
(74) Attorney, Agent, or Firm—Mattingly, Stanger & Malur

(57) ABSTRACT

A biomagnetic field measurement apparatus comprises, a plurality of magnetometers each having a SQUID sensor and a detection coil and each detecting a magnetic field generated from a heart of a fetus in a mother; a processor processing magnetic field wave forms detected by the magnetometers; and a display displaying results obtained by the processor. The processor estimates a position of a current dipole from the magnetic field wave forms, and processes projecting the position of the current dipole on a first plane parallel to a plane on which one ends of the magnetometers are disposed on processes projecting the position of the current dipole on a second plane perpendicular to the plane on which the one ends of the magnetometers are disposed. The position of the current dipole projected on the first plane and the position of the current dipole projected on the second plane are displayed on the display.

32 Claims, 23 Drawing Sheets

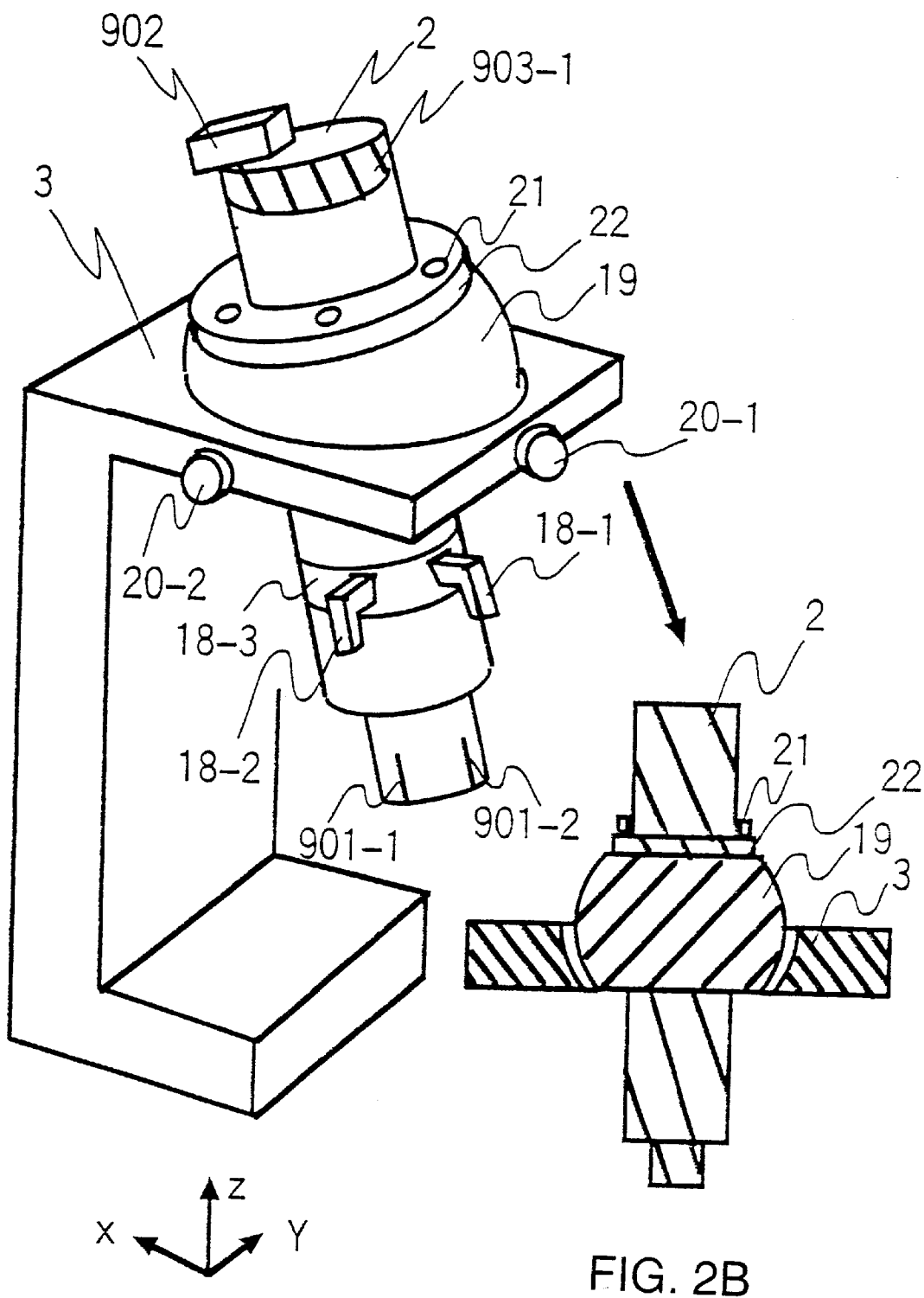

BIOMAGNETIC FIELD MEASUREMENT APPARATUS

BACKGROUND OF THE INVENTION

The present invention relates to a magnetic field measurement apparatus using a SQUID (Superconducting Quantum Interference Device) for measuring a very small magnetic field generated from hearts and brains of an adult, an infant and a fetus or the like, and particularly to a biomagnetic field measurement apparatus for displaying a magnetic field wave form generated from a heart of a fotus and the position of the heart of the fotus.

When a biomagnetic field measured by a conventional biomagnetic field measurement apparatus is displayed, it is customary that a magnetic wave form is displayed at every channel as it is or a contour map at a certain time point is displayed. Also, there is known a Dewar apparatus in which a sensor position can be finely adjusted easily and freely in accordance with a subject to be inspected or the like (Japanese Patent Laid-open No.297456/1995).

SUMMARY OF THE INVENTION

According to the prior art, when a position of a heart of a fotus is moved within a womb by the movements of the fotus, as a method of monitoring the movements of the fotus and heart rate, there are known a delivery monitor apparatus (Handbook of Clinical Engineering, pp.474–475 (1984)) and a ultrasonic diagnosis apparatus. There is not realized a method of measuring a fotus based on a magnetic wave form obtained by a biomagnetic field measurement apparatus. There is then the problem that it is difficult to understand an aging change of the health of a fotus. An object of the present invention is to provide a biomagnetic field measurement apparatus in which a position of a current dipole (hereinafter simply referred to as a dipole) is estimated and the dipole is displayed on a monitor as a position of a heart of a fotus, thereby resulting in the movements of the fotus and the variation of the heart rate being observed.

According to the present invention, there is provided a biomagnetic field measurement apparatus which is comprised of a plurality of magnetometers each having a SQUID sensor and a detection coil and each detecting a magnetic field generated from a heart of a fotus in a mother, a processor processing magnetic field wave forms detected by the magnetometers and a display displaying results obtained by the processor, wherein the processor estimates a position of a current dipole from the magnetic field wave forms, and processes projecting the position of the current dipole on a first plane parallel to a plane on which one ends of the magnetometers are disposed and processes projecting the position of the current dipole on a second plane perpendicular to the plane on which the one ends of the magnetometers are disposed, and wherein the position of the current dipole projected on the first plane and the position of the current dipole projected on the second plane are displayed on the display. More in detail, the processor executes the processing for estimating the position of the dipole from the magnetic field wave form and the processing in which the position of the dipole is expressed as the position of the heart of the fotus and the position of the dipole is projected onto the plane parallel to and perpendicular to the plane (or the bottom surface of the cryostat for housing magnetometers) in which the tip end portions of a plurality of magnetometers are disposed, and the display means displays results obtained when the position of the dipole is projected onto the parallel plane and the vertical plane.

The biomagnetic field measurement apparatus according to the present invention has the following characteristics: (1) estimating the position of one dipole from the magnetic field wave form; (2) estimating the position of the dipole at a time point in which the peak value of the magnetic wave form is detected; (3) display means displays a plane of (x, y, z) space on which the position of the dipole is projected; (4) display means projects results obtained when the magnetometer is projected onto the parallel plane and the perpendicular plane; (5) display means displays a time change of the position of the dipole, and display means displays a route indicating the time change of the position of the dipole; (6) display means displays the route indicating the time change of the position of the dipole with numerals; (7) display means displays the route indicating the time change of the position of the dipole with arrows; (8) display means displays the position of the dipole by changing the color depending on the magnitude of the dipole; (9) display means displays a movement speed of the position of the dipole; (10) display means displays a movement distance of the position of the dipole; (11) display means displays a rotation amount in the direction of the dipole; (12) display means displays the time change of the heart rate of the fotus calculated from the magnetic field wave form; (13) display means displays a power spectrum of a time change of a heart rate of a fotus calculated from the magnetic field wave form. (14) Each magnetometer has detection coils formed on one bobbin for detecting components of three directions perpendicular to each other in magnetic field, and tip end portions of a plurality of the bobbins are disposed in a matrix fashion. (15) Display means displays magnetic field wave forms in response to the layout of the tip end portions of a plurality of bobbins. (16) Display means displays components of three directions perpendicular to each other detected by each magnetometer of a plurality of magnetometers on different regions at every direction of the three directions. (17) The processor executes any of the filtering for eliminating a noise lower than or equal to 5 Hz to 6 Hz (e.g. 1 Hz, 2 Hz, 3 Hz) generated in accordance with respiration of a mother, the adding processing of magnetic field wave forms and the peak detection processing of magnetic field wave forms.

As described above, the state of the movements of the foetus can be easily monitored from the position and the state of the heart of the fetus displayed on the display in a two-dimensional fashion and the variation of the heart beat can be analyzed with ease.

A biomagnetic field measurement apparatus comprises a plurality of magnetometers each detecting magnetic field generated from a subject to be inspected, a cryostat which holds the magnetometers at a low temperature by a cooling liquid, a member holding the cryostat and a spherical member in which the cryostat is installed, wherein the member holding the cryostat has a hole in which the spherical member can rotate.

Also, a biomagnetic field measurement apparatus comprises a plurality of magnetometers each detecting magnetic field generated from a subject to be inspected and a cryostat which holds the magnetometers at a low temperature by a cooling liquid, wherein a member having humidity is disposed on a part of the cryostat, or a heating member is disposed on a part of the cryostat. Further, a biomagnetic field measurement apparatus comprises a bag-like member for capturing a cooling gas evaporated from the inside of the cryostat on the upper portion of the cryostat and a member for filling a gas generated from the cooling liquid in the cryostat at an upper part of the cryostat.

Also, a biomagnetic field measurement apparatus comprises a plurality of magnetometers each detecting magnetic field generated from a subject to be inspected, a cryostat which holds the magnetometers at a low temperature by a cooling liquid and a member holding the cryostat, wherein, in the cryostat, a first tube for introducing the cooling liquid into the cryostat and a second tube which has a shape of a funnel tube at one end and into which one end of the first tube can be inserted.

Further, a biomagnetic field measurement apparatus comprises a plurality of magnetometers each having a SQUID sensor and a detection coil and each detecting magnetic field generated from a subject to be inspected, a cryostat which holds the magnetometers at a low temperature by a cooling liquid, a holding member which holds the cryostat such that the cryostat can be rotatable about an axis of the cryostat, a position fitting member which has a shape the same as a part of a shape including a center of a bottom surface of the cryostat and has a plurality of poles for contacting a peripheral surface near the bottom surface of the cryostat and a weight marker which is connected to the position fitting member by string, at a position of the weight marker corresponding to the center of the bottom surface of the cryostat.

Further, the present invention is featured in a biomagnetic field measurement method having the following arrangements:

(C1) A biomagnetic field measurement method comprising the steps of a step detecting magnetic field generated from a fetus in a mother by a plurality of magnetometers each having a SQUID sensor and a detection coil, a step for processing magnetic field wave forms detected by the magnetometers, and a step for displaying results on the display, wherein the processing process estimates a position of a current dipole from the magnetic field wave forms, and processes projecting the position of the current dipole on a plane parallel to a plane on which one ends of the magnetometers are disposed and processes projecting the position of the current dipole on a plane perpendicular to the plane on which the one ends of the magnetometers are disposed, and wherein the position of the current dipole projected on the parallel plane and the position of the current dipole projected on the perpendicular plane are displayed on the display.

(C2) In the method described in (C1), the processor estimates a position of one current dipole from the magnetic field wave forms.

(C3) In the method described in (C1), the processor estimates the position of the current dipole from the magnetic field wave forms when peaks of the magnetic wave forms are detected.

(C4) In the method described in (C1), planes in a space (x, y, z) projecting the position of the current dipole are displayed on the display.

(C5) In the method described in (C1), positions of the one ends of the magnetometers projected on the first parallel plane and the second perpendicular plane are displayed on the display.

(C6) In the method described in (C1), a time variation of the position of the current dipole is displayed on the display.

(C7) In the method described in (C1), a path showing a time variation of the position of the current dipole is displayed on the display.

(C8) In the method described in (C1), a path showing a time variation of the position of the current dipole is displayed on the display, and the path is displayed with a number.

(C9) In the method described in (C1), a path showing a time variation of the position of the current dipole is displayed on the display, and the path is displayed with an arrow.

(C10) In the method described in (C1), the position of the current dipole is displayed on the display, a change of a magnitude of the current dipole is displayed by a change of a color.

(C11) In the method described in (C1), a moving velocity of the position of the current dipole is displayed on the display.

(C12) In the method described in (C1), a moving distance of the position of the current dipole is displayed on the display.

(C13) In the method described in (C1), an amount of rotation in a direction of the current dipole is displayed on the display.

(C14) In the method described in (C1), a time variation of a heart rate of the fetus is displayed on the display, and the heart rate of the fetus is obtained from the magnetic field wave forms.

(C15) In the method described in (C1), a power spectrum of a time variation of a heart rate of the fetus is displayed on the display, and the heart rate of the fetus is obtained from the magnetic filed wave forms.

(C16) In the method described in (C1), each of the magnetic field wave forms corresponding to each position of the one ends of the magnetometers is displayed on the display.

(C17) In the method described in (C1), three components of the magnetic field generated from the heart of the fetus in three directions are displayed on the display in a different region for each component of the three components.

(C18) In the method described in (C1), the processor processes a filtering process for removing a noise having frequencies less than or equal to 5 Hz to 6 Hz (e.g. 1 Hz, 2 Hz, 3 Hz) generated from respiration of the mother, or an adding process, or a peak detection process of the magnetic field wave forms.

The present invention will be summarized with reference to FIG. 1 as follows. A biomagnetic field measurement apparatus comprises a plurality of magnetometers each having a SQUID sensor and a detection coil and each detecting a magnetic field generated from a heart of a fetus in a mother, a processor processing magnetic field wave forms detected by the magnetometers and a display displaying results obtained by the processor, wherein the processor 6 estimates a position of a current dipole from the magnetic field wave forms, and processes projecting the position of the current dipole on a plane 12 parallel to a plane on which one ends of the magnetometers are disposed and processes projecting the position of the current dipole on a plane 13 perpendicular to the plane on which the one ends of the magnetometers are disposed, and wherein the position of the current dipole projected on the plane 12 and the position of the current dipole projected on the plane 13 are displayed on the displays 6, 7. As a result, it is possible to provide a biomagnetic field measurement apparatus in which the movements of the position of the heart of the fetus can be monitored and in which the state of the heart of the foetus can be detected.

BRIEF DESCRIPTION OF THE DRAWINGS

FIG. 2A is a perspective view showing a gantry section of the biomagnetic field measurement apparatus according to the embodiment of the present invention, and FIG. 2B is a cross-sectional view thereof;

DETAILED DESCRIPTION OF THE PREFERRED EMBODIMENTS

Figure 1A:
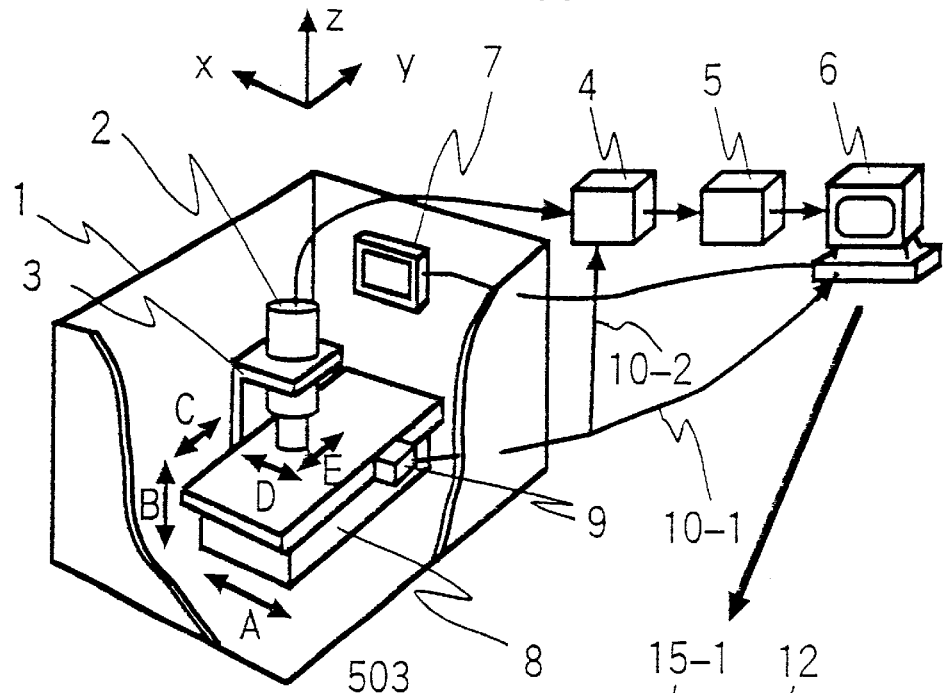
FIG. 1A is a perspective view showing an example of a constitution of a biomagnetic field measurement apparatus according to an embodiment of the present invention, and a diagram showing an example of a displayed picture.
Figure 1B:
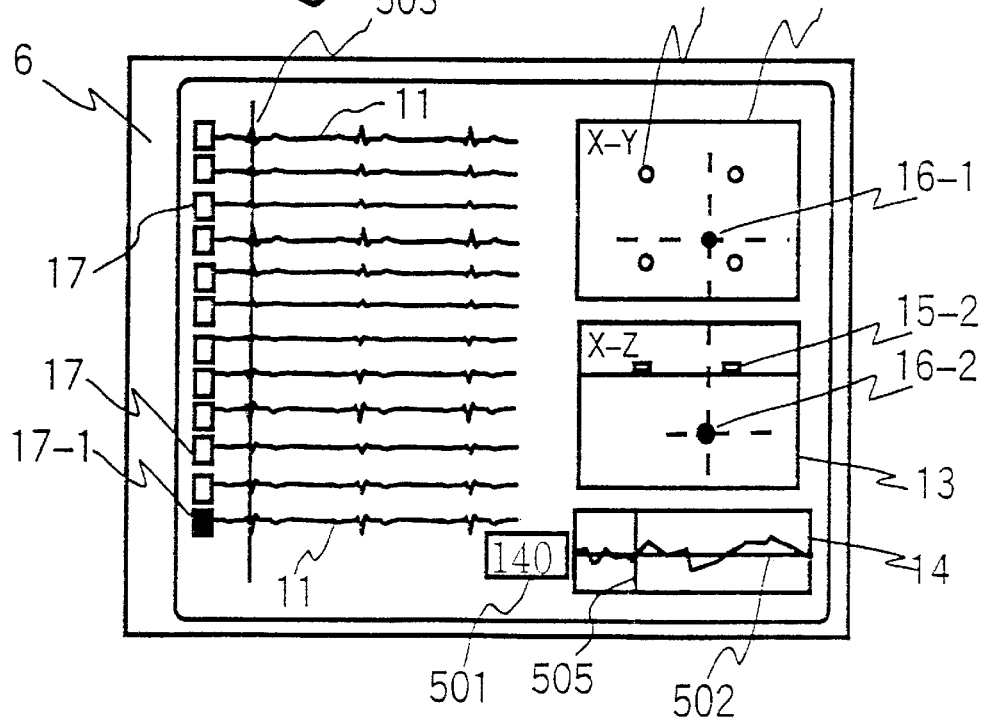

FIG. 1A is a perspective view illustrating an example of a biomagnetic field measurement apparatus according to an embodiment of the present invention and FIG. 1B is a diagram showing an example of a displayed picture. As shown in FIG. 1A, within the shielded room 1, there are disposed a bed 8 on which a subject to be inspected (not shown, such as a pregnant woman) lays herself, a cryostat 2 for storing cooling liquid (liquid helium or liquid nitrogen) in order to hold the magnetometers in a superconducting state, a gantry 3 for mechanically holding the cryostat 2, and a monitor apparatus 7 baa which magnetic field wave forms or the like can be monitored in the inside of the shielded room 1. As the monitor apparatus 7, there is used a liquid-crystal display and the liquid-crystal display displays a variety of data converted into video signals. The bed 8 can be moved in the x direction (A direction), the y direction (C direction) and the z direction (B direction). The gantry 3 can be rotated within the x-z plane (D direction) and the y-z plane (E direction). In the outside of the shielded room 1, there are disposed a magnetometer driving circuit 4, an amplifier filter unit 5 and a computer 6 for collecting data and executing a computation.

A method of operating the biomagnetic field measurement apparatus shown in FIG. 1 will be described in brief. When the operator of the apparatus operates a control button 9, the magnetometer driving circuit 4, the amplifier filter unit 5 and the computer 6 are operated under control of control signals 10-1, 10-2 so that the computer 6 starts to collect data. Then, while monitoring results displayed on the monitor apparatus 7 disposed at the position distant from the cryostat 2 or disposed at the wall surface of the shielded room 1, the operator adjusts the positional relationship between the bed 8 and the gantry 3, and adjusts the positional relationship between the bottom surface of the cryostat 2 and the abdomen surface of a pregnant woman so that magnetic fields generated from the heart of a fetus may be detected with high sensitivity. Specifically, while monitoring the magnetic field wave form displayed on the monitor apparatus 7, the operator closely contacts the bottom surface of the cryostat 2 and the abdomen surface of the pregnant woman at the optimum position in which magnetic field wave forms can be detected with high sensitivity.

After the above-mentioned optimum position is obtained, the operator sets a time in which magnetic fields are detected and data are collected or the like by the control button 9. Then, when the operator controls the collected start by the control button 9, magnetic field wave forms are read in the computer 6 as digital signals. Data indicating the collected magnetic field wave forms and data indicating processed results are displayed on the display screen of the monitor apparatus 7 as well as the display screen of the computer 6.

Then, the operator selects a channel (channel means magnetic field wave forms detected by individual magnetometers and magnetic field wave forms of 12 channels in total are displayed in the example shown in FIG. 1B) in which the magnetic field wave form with highest sensitivity in magnetic field wave forms 11 is selected by using selection button 17 (button 17-1 is selected in the example shown in FIG. 1) for selecting a desired channel. Then, the operator sets a trigger level for detecting the peak by the selected channel. When the movements of the fetus and the variation of the heart beat are monitored, the computer 6 detects the peak and estimates the magnitude and existence position of the dipole. Then, the operator can diagnose the fetus with reference to the heart position and the variation of the heart beat thus displayed. When the operator continues the diagnosis further, the operator can measure magnetic field wave forms continuously in the shielded room 1.

On the display screens of the monitor apparatus 7 and the computer 6, there are displayed the magnetic field wave form 11, the waveform selection button 17 for selecting a desired channel from a plurality of channels, a projected picture 12 on the x-y plane of the heart of the estimated fetus, a projected picture 13 into the y-z plane or the x-z plane of the position of the heart of the estimated fetus, a plotted picture of the variation of the heart beat of the fetus and a picture 501 of average value of heart rate. Incidentally, the x-y plane displayed on the display screen is the bottom surface of the cryostat 2 with which the abdomen surface of the pregnant woman is closely contacted. The z axis is parallel to the center axis of the cryostat 2, and the y-z plane and the x-z plane are planes perpendicular to the x-y plane.

Figure 16:
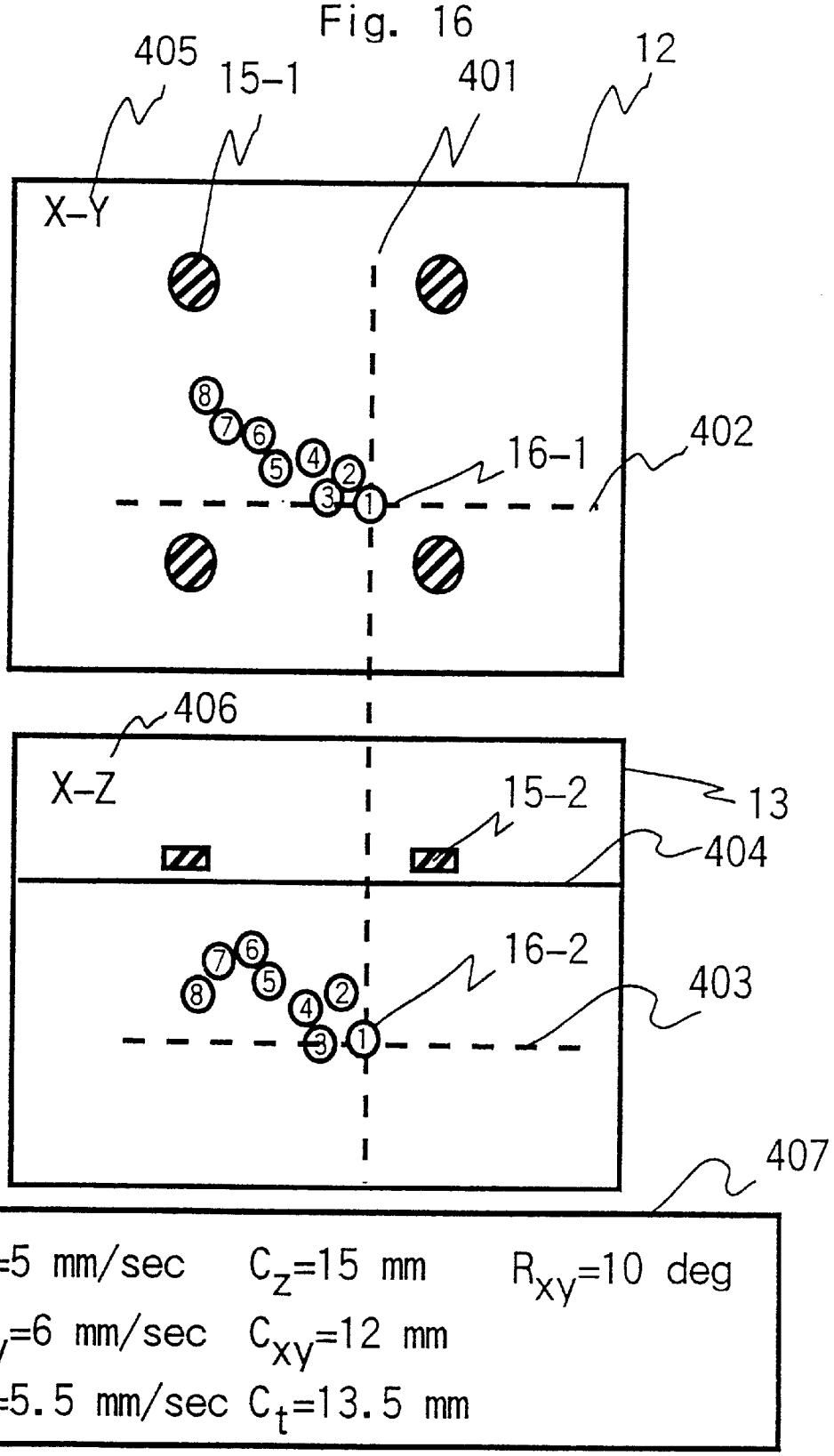
FIG. 16 is a diagram showing an example of a picture screen for displaying the position of the heart of a fetus in the biomagnetic field measurement apparatus according to the embodiment of the present invention.

Projection positions 16-1, 16-2 of the heart of the fetus at a time point (this time point is the same as the time point of a display line 505 shown in a heart rate variation plot picture 14) of a display line 503 shown in the magnetic field wave form 11 are shown by solid-circles in the projected pictures 12 and 13. Further, a projection position 15-1 onto the x-y plane of the position of the magnetometer and a projection position 15-2 onto the y-z plane or the x-z plane of each magnetometer are shown by open circles in the projected pictures 12 and 13 (the positions of four magnetometers are illustrated in the example shown in FIG. 1B). Also, a horizontal line and a vertical line passing the center of the solid-circle indicating the position of the heart of the fetus are shown on the projection picture 12 and the projection picture 13 by dotted lines. The plotted picture 14 of the variation of the heart beat shows the variation of the heart beat of the whole time zone in which magnetic field wave forms are detected, and a display line 502 indicating the average value of the variation of the heart beat is displayed in the plotted picture 14. The magnetic field wave form 11 is continuously displayed during a time zone of three heart beats. Incidentally, the display of the position of the heart of the fetus will be described later on (FIG. 16).

FIG. 2A is a perspective view and FIG. 2B is a cross-sectional view showing the gantry 3 for mechanically holding the cryostat 2 in the biomagnetic field measurement apparatus according to the embodiment of the present invention. As shown in FIG. 2, the cryostat 2 is fixed to a spherical moving member 19 by a fixing screw 21. The spherical moving member 19 is attached to a hole having the same curvature as that of a spherical member in the inside of the gantry 3. The spherical moving member 19 can freely be rotated in the inside of the gantry 3, thereby making it possible to set the cryostat 2 at an arbitrary angle.

After the operator rotates the cryostat 2 at a desired measurement angle by using handles 18-1, 18-2 and set the angle, the operator fixes the rotation of the cryostat 2 by stoppers 20-1, 20-2. Also, the handles 18-1, 18-2 may be disposed at the position perpendicular to a handle attachment portion 18-3, whereby the handle 18-1, for example, may be used as a means for moving the cryostat 2 along the x-z plane and the handle 18-2 may be used as a means far moving the cryostat 2 along the y-z plane. Thus, the cryostat 2 can be set to an arbitrary angle with ease. The handles 18-1, 18-2 and the handle attachment portion 18-3 should preferably be made of plastic materials as a nonmagnetic material.

On the upper portion of the cryostat 2, there are disposed a sponge 903-1 for preventing moisture on the upper portion of the cryostat 2 from being dropped onto the subject to be inspected and a connector box 902 for transmitting a signal from the magnetometers to the outside of the shielded room 1. On the lower portion of the cryostat 2, there are formed display lines 901-1 and 901-2 for indicating the orientation of the cryostat 2. The display line 901-1, for example, is displayed by a black line, and the display line 901-2 is displayed by a red line. Thus, when the display lines 901-1 and 901-2 are disposed at the positions perpendicular to each other, it is possible to detect the orientation of the cryostat 2 with ease.

Figure 3A:
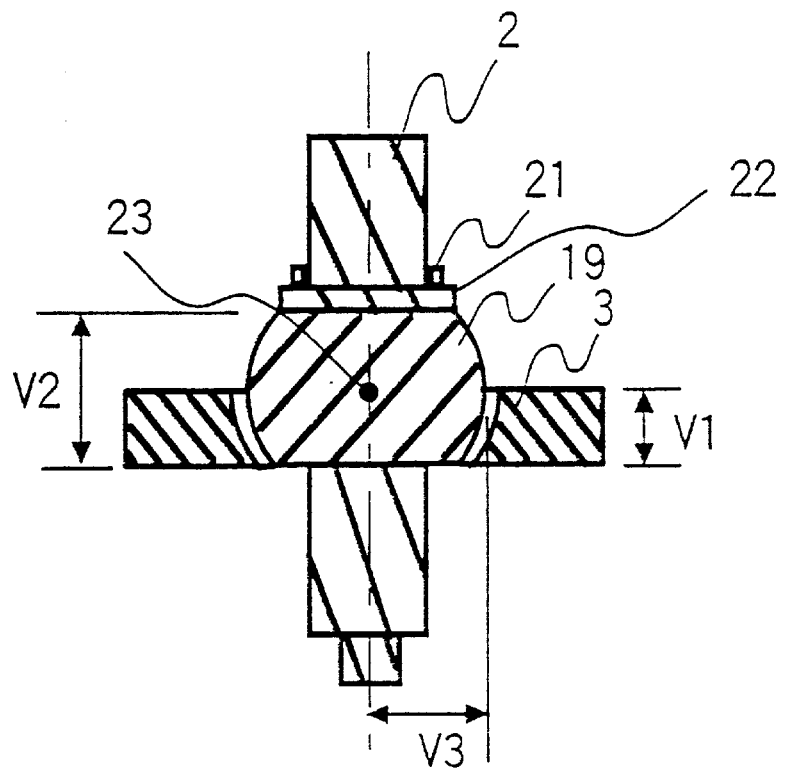
FIGS. 3A and 3B are cross-sectional views showing in detail a rotation mechanism of a cryostat 2 shown in FIGS. 2A and 2B according to the embodiment of the present invention.
Figure 3B:
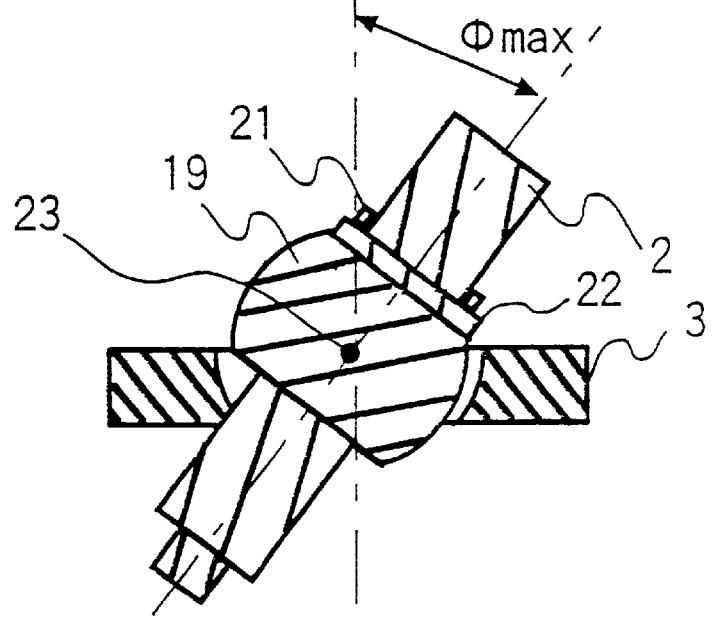

FIGS. 3A and 3B are cross-sectional views showing a rotation mechanism of the cryostat 2 shown in FIG. 2. FIG. 3A shows the state in which the cryostat 2 is set in the vertical state, and FIG. 3B shows the state in which an inclination angle of the cryostat 2 is maximum. V1 is the thickness of the gantry 3, V2 is the thickness of the spherical moving member 19 and $\Phi$ is the inclination angle of the cryostat 2. Here, if $V1 \geq (V2/2)$, then the spherical moving member 19 uniformly contacts with the gantry 3 so that the movement of the spherical moving member 19 can become smooth, thereby making it possible to maintain safety.

The present invention will now be described in the case where a center point of the spherical moving member 19 is located flush with the upper surface of the gantry 3, i.e. $V1=(V2/2)$. In order to reduce the size of the spherical moving member 19 as much as possible, a maximum diameter of a guard portion 22 integrally formed with the cryostat 2 and a diameter of the upper portion surface of the spherical moving member 19 are made substantially the same. That is, the outer configuration of the upper portion surface of the spherical moving member 19 and the outer configuration of the guard portion 22 are substantially the same. At that time, the inclination angle $\Phi$ of the cryostat 2 becomes maximum when the guard portion 22 contacts with the upper surface of the gantry 3 if the cryostat 2 is inclined. Assuming that V3 is a radius of a ball of the spherical moving member 19, then a maximum inclination angle $\Phi_{max}$ is presented as $\Phi_{max}=\sin^{-1}(V1/V3)=\sin^{-1}((V2/2)/V3)$.

When V3=175 mm and V1=(V2/2)=50 mm, the maximum inclination angle $\Phi_{max}$ becomes about 17°. As the inclination angle of the cryostat 2 increases, an area of a liquid helium surface which is in contact with vapor helium increases so that a temperature difference in the inside of the cryostat 2 increases. There then arises a problem that an amount of liquid helium being evaporated increases. To solve this problem, the maximum inclination angle $\Phi_{max}$ should preferably be set within a range of 15° to 30°. In this embodiment, the maximum inclination angle $\Phi_{max}$ is set to 30° to enable the cryostat 2 to be inclined (tilted) in an arbitrary direction so that the bottom portion of the cryostat 2 may be rapidly positioned at the optimum position of the abdomen of a mother's body from which magnetic fields from the heart of the fetus are detected.

With respect to the performance of the cryostat, it is important for the cryostat to hold the liquid helium during a long period of time. That is, a time interval from the supply of the liquid helium to the next supply of the liquid helium is important. The holding time of the liquid helium is determined based on the outer configuration dimension of the cryostat and an evaporation quantity (evaporation rate)

of liquid helium depending upon the inside structure or the like. Although the outer configuration dimension of the cryostat depends upon an object to be measured and a measurement method, in order for the SQUID magnetometer to detect the signal with high intensity of the magnetic field, the thickness (distance in the axis direction of the cryostat between the outer side surface of the outer tube container and the inner tube container) of the bottom surface of the cryostat should be reduced so that the detection coil can be made close to the object to be measured as much as possible.

Figure 4:
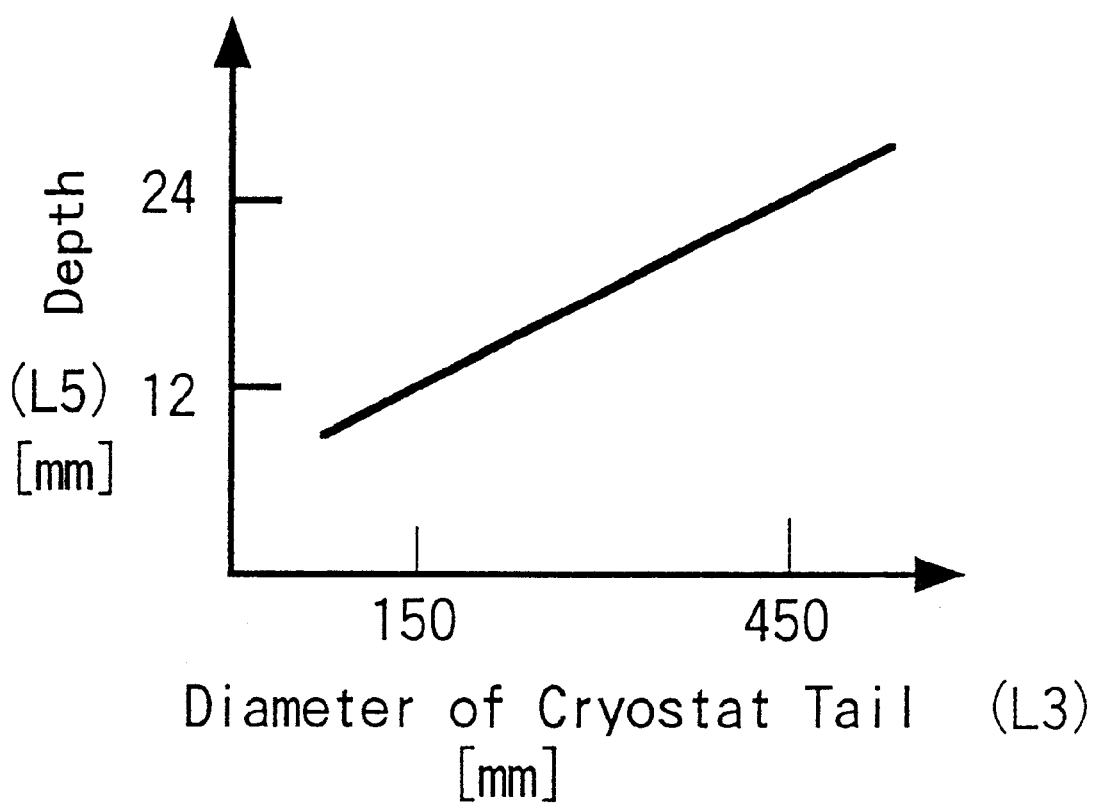
FIG. 4 is a diagram showing a relationship between a diameter of a bottom of a cryostat and a thickness of a bottom of a cryostat according to the embodiment of the present invention.
Figure 5:
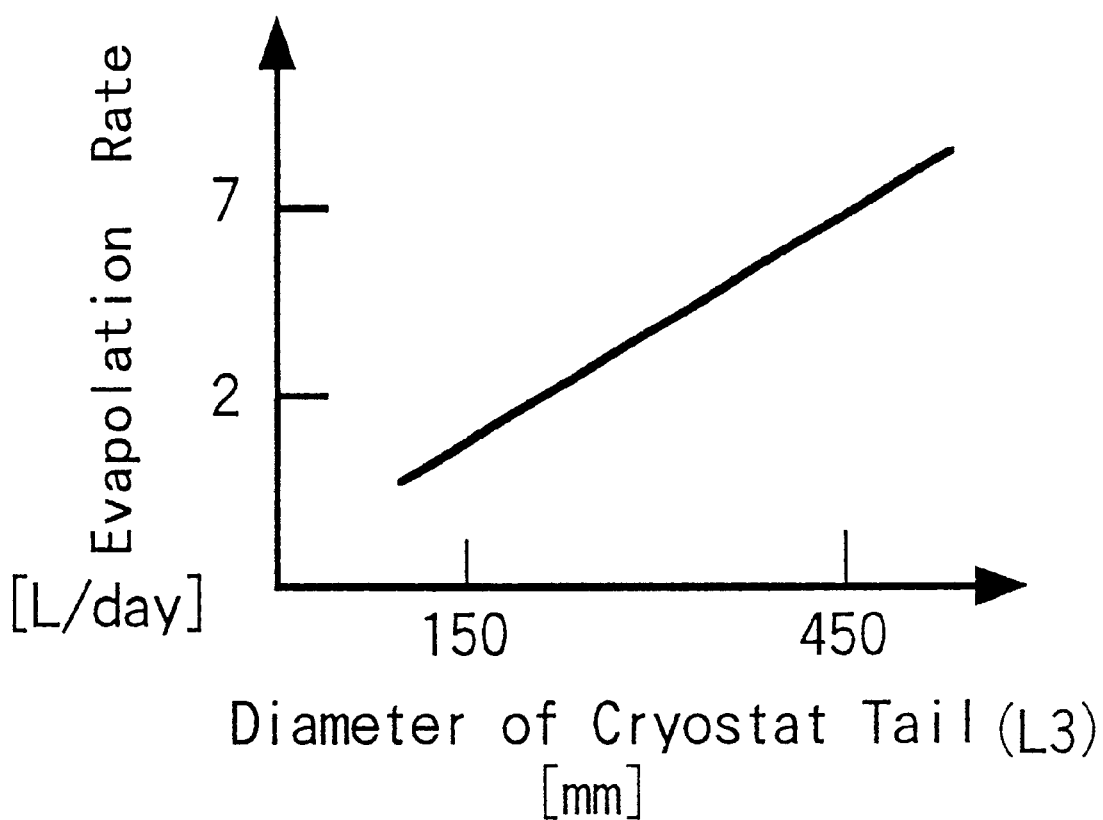
FIG. 5 is a diagram showing a relationship between a diameter of a bottom of a cryostat and an evaporated amount of liquid helium according to the embodiment of the present invention.
Figure 6:
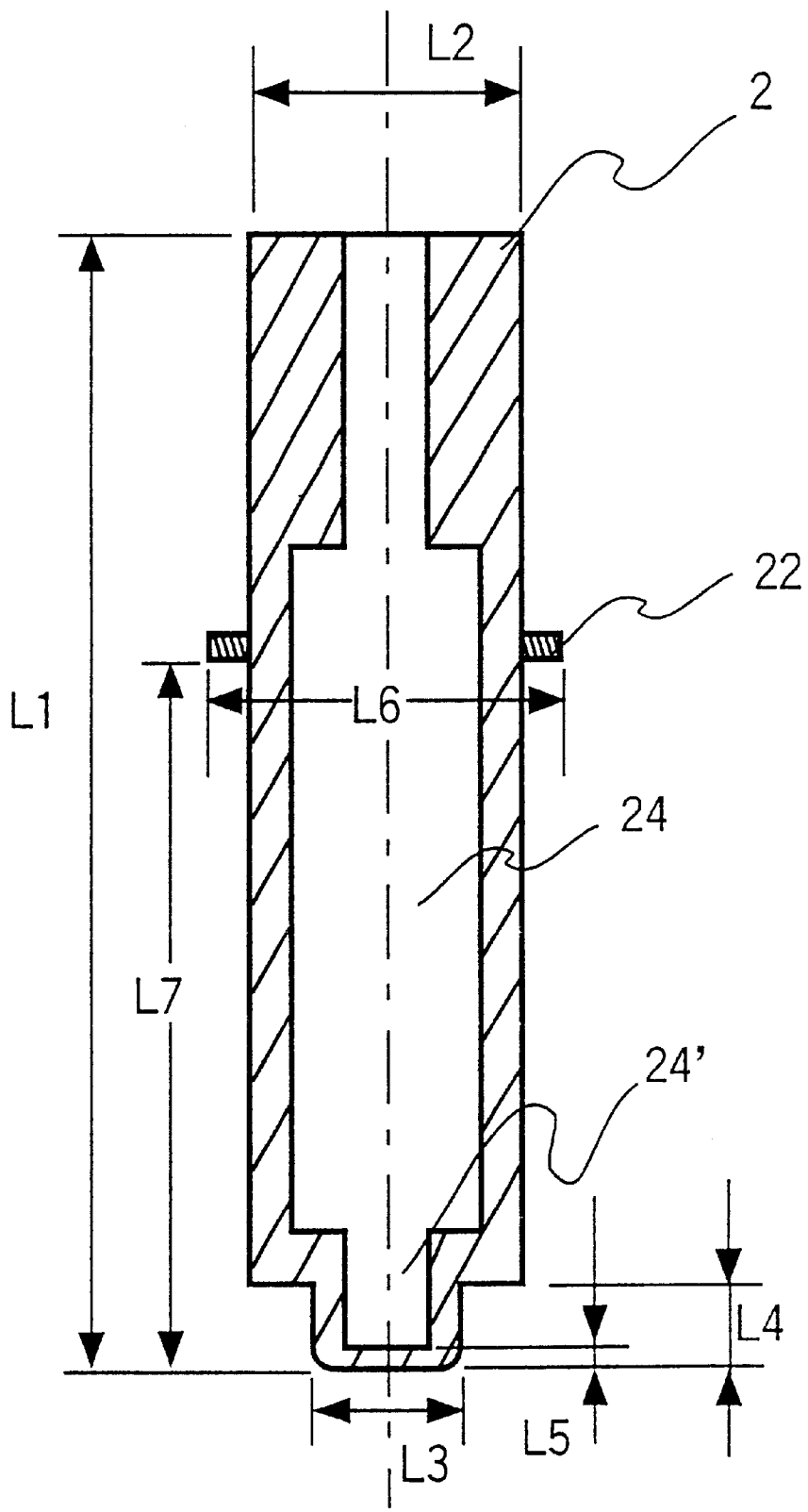
FIG. 6 is a cross-sectional view showing in detail the outer shape of the cryostat shown in FIGS. 2A and 2B.

FIG. 4 is a diagram showing a relationship between the diameter (L3 shown in FIG. 6) of the bottom surface of the cryostat and the thickness (L5 shown in FIG. 6) of the bottom surface of the cryostat according to this embodiment. FIG. 5 is a diagram showing a relationship between the diameter (L3 shown in FIG. 6) of the bottom surface of the cryostat and the evaporation quantity of liquid helium according to this embodiment. FIG. 6 is a cross-sectional view showing the outer shape of the cryostat 2 shown in FIGS. 2A and 2B in detail.

Since the spacing between the outer tube container and the inner tube container of the cryostat is held in the vacuum state in order to keep insulation from heat, a relationship between the diameter (L3) and the thickness (L5) of the bottom surface of the cryostat shown in FIG. 4 is determined mainly a standpoint of safety considering a pressure-resistant efficiency. That is, when then diameter (L3) of the bottom surface is large, if the thickness (L5) of the bottom surface is not increased, then the pressure-resistant property cannot be maintained. Since the thickness of the bottom surface of the cryostat is changed with the thickness of the material such as an FRP comprising the outer tube container and the inner tube container of the cryostat and a method of filling adiabatic material disposed between the outer tube container and the inner tube container, FIG. 4 shows an average relationship obtained empirically. The relationship shown in FIG. 5 is a relationship obtained when the thickness of the bottom surface of the cryostat is changed arbitrarily. Similarly to FIG. 4, FIG. 5 shows an average relationship obtained empirically.

A study of FIGS. 4 and 5 reveals that, as the diameter of the bottom surface of the cryostat is decreased, the thickness of the bottom surface of the cryostat can be reduced and also the evaporation quantity of the liquid helium can also be decreased. That is, in the cryostat in which the diameter of the bottom surface is small, if such cryostat is arranged such that it can store the same liquid helium quantity as the liquid helium quantity used in the cryostat in which the diameter of the bottom surface is large, then the evaporation quantity of the liquid helium is small, and hence the time for storing the liquid helium can be extended.

FIG. 6 shows an example of the arrangement of the above-mentioned cryostat 2 having a long storing time of liquid helium. In the example shown in FIG. 6, the length of the cylindrical cryostat 2 is presented as L1=1095 mm, the upper portion diameter is presented as L2=256 mm, the diameter of the bottom surface is presented as L3=150 mm, the length in which the whole of a sensor unit is inserted is presented as L4=80 mm, the thickness of the bottom surface is presented as L5=12 mm which is half of the conventional apparatus, the maximum diameter of the guard portion 22 is presented as L6=335 mm, and the length from the bottom surface to the lower surface of the guard portion 22 is presented as L7=700 mm. That is, in order to reduce the thickness of the bottom portion of the cryostat in such a manner that the detection coil may be located close to the heart of the fetus, the area of the bottom portion of the cryostat should be reduced. The bottom surface diameter L3=150 mm and the bottom surface thickness L5=12 mm can satisfy the relationship shown in FIG. 4. In the example shown in FIG. 6, from a relationship shown in FIG. 5, it becomes possible to decrease the evaporation quantity of the liquid helium under 1.6 L (liter)/(lay.

Figure 12:
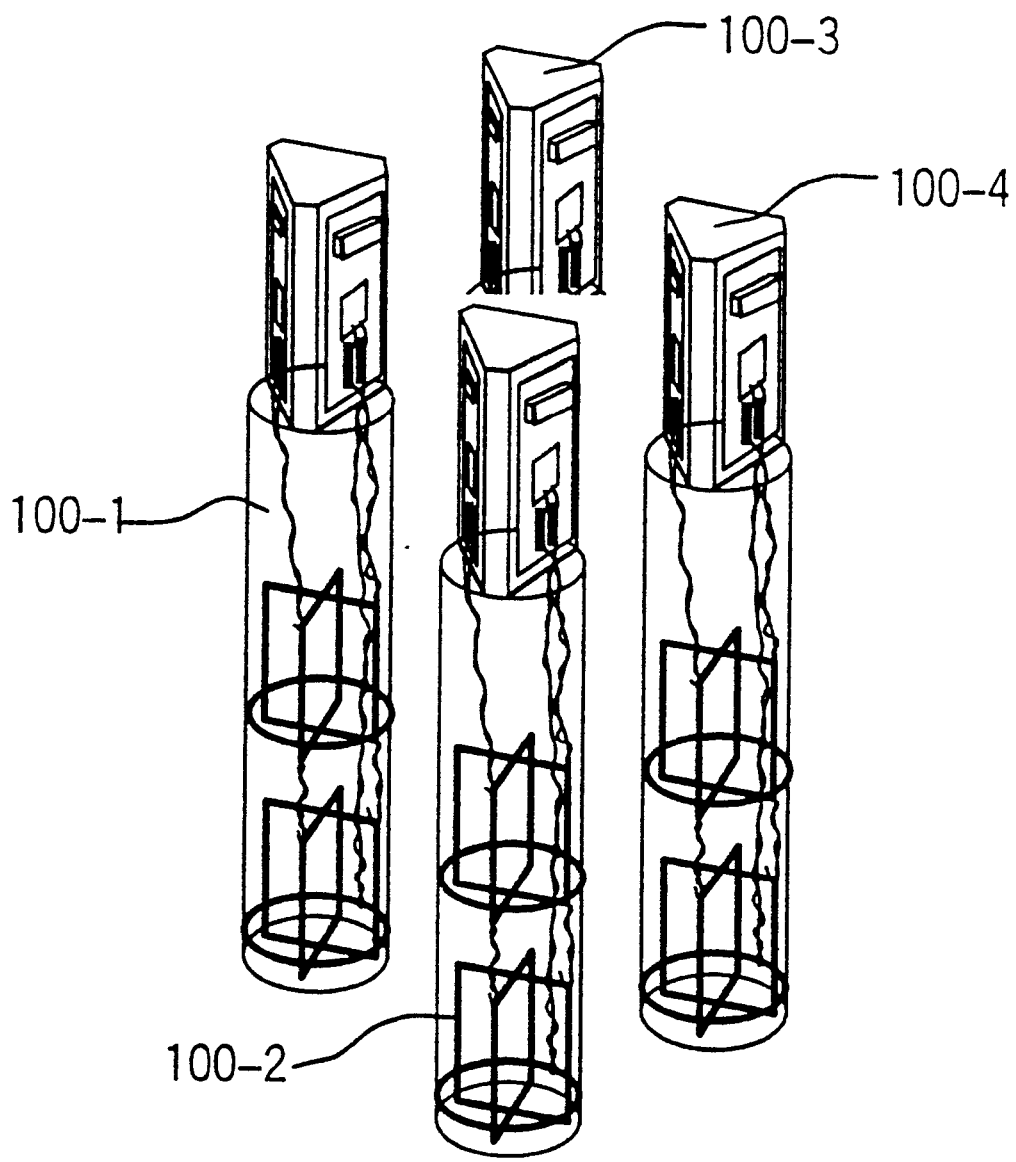
FIG. 12 is a perspective view illustrating a manner in which the magnetometers used in the biomagnetic field measurement apparatus according to the embodiment of the present invention are arrayed.

The length L4 into which the whole of the sensor unit can be inserted should preferably be selected to be a distance long enough so that the whole of the sensor unit may be inserted into the inside of a lower region 24' of the liquid helium tank portion 24 so as to hold the SQUID sensor shown in FIG. 12 at an extremely low temperature state (superconducting state) and that the operator may visually confirm the positioning between the bottom surface of the cryostat and the subject to be inspected from the position at which the operator stands. In this embodiment, L4=80 mm.

As earlier described, if the storage quantity of the liquid helium is increased, then the storing time (time in which the sensor is able to operate) of the liquid helium can be extended, and the number of supplementing the liquid helium can be reduced, thereby making it possible to alleviate the time and work of the worker. In the example shown in FIG. 6, the capacity of the liquid helium tank portion 24 can be increased by increasing L1 and L7. When the biomagnetic field measurement apparatus is arranged such that it can store the liquid helium of about 17L (liters), if the evaporation amount of the liquid helium is set to be less than 1.6 L (liters)/day as shown in FIG. 5, then it is possible tD realize the liquid helium holding time (time in which the sensor is able to operate) longer than 10 days. In this embodiment, the liquid helium evaporation quantity that was confirmed in actual practice was 1.2 L (liter)/day. Under general conditions in which the biomagnetic field measurement apparatus was in use, the biomagnetic field measurement apparatus could continuously measure magnetic field wave forms during a period of time ranging from 10 days to about two weeks, and the filling of the liquid helium was unnecessary. Incidentally, the guard portion 22 for holding the cryostat 2 at the gantry 3 is fixed to the cryostat 2 by an adhesive.

Figure 7:
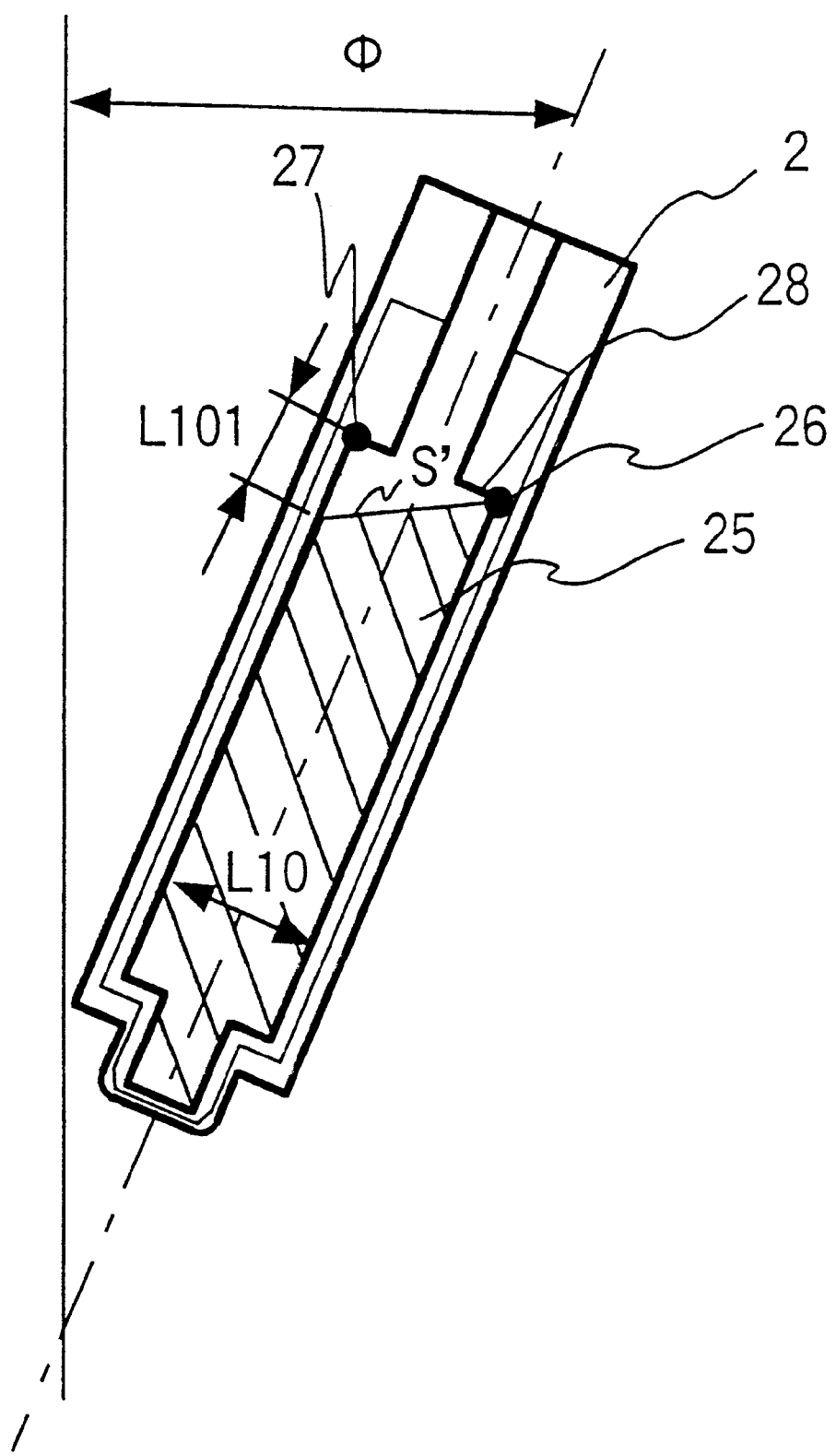
FIG. 7 is a cross-sectional view illustrating a manner in which the cryostat in which liquid helium is stored is inclined by an inclination angle Φ.

FIG. 7 is a cross-sectional view illustrating the biomagnetic field measurement apparatus obtained when the cryostat 2 for storing the liquid helium 25 is inclined by an inclination angle $\Phi$ ($\Phi=\tan^{-1}(L101/L10)$). When the cryostat 2 is inclined, the upper surface of the Liquid helium forms a surface S' which connects a lower point distant from the upper portion position 27 of the tank portion by the distance L101 and the upper portion position 26 of the tank portion. If the liquid helium is much more stored in excess of the surface S', then the liquid helium contacts with an upper portion plate 28 connecting the upper portion position 26 or 27 of the tank portion at the position higher than the upper portion position 26 or 27 of the tank portion. As a result, the liquid helium is evaporated more rapidly, and the upper surface of the liquid helium is settled on the surface S' shown in FIG. 7 in a short period of time. Accordingly, when the cryostat 2 is inclined by the maximum inclination angle $\Phi_{max}$, the filling quantity of the liquid helium should be adjusted in such a manner that the liquid level obtained when the liquid helium is filled may be lowered from the upper portion position 26 or 27 of the tank portion by (L101)/2.

That is, according to the arrangement in which the maximum liquid level of the liquid helium may be disposed at the position lower than the upper portion plate 28 having the same outer shape as the size of the maximum inner diameter L10 of the tank portion of the liquid helium by $(L10) \cdot (\tan^{-1}\Phi_{max})/2$ when $\Phi_{max}$ assumes the maximum inclination angle of the cryostat 2, L10 assumes the maximum inner diameter of the tank portion of the liquid helium and the cryostat 2 is held in the vertical direction, it is possible to fill liquid helium of an optimum quantity into the cryostat 2. As a result, even when the cryostat 2 is inclined by the maximum inclination angle $\Phi_{max}$, the liquid level of the liquid helium does not contact with the upper portion plate 28 of the tank portion so that the liquid helium can be prevented from being evaporated rapidly.

Figure 8:
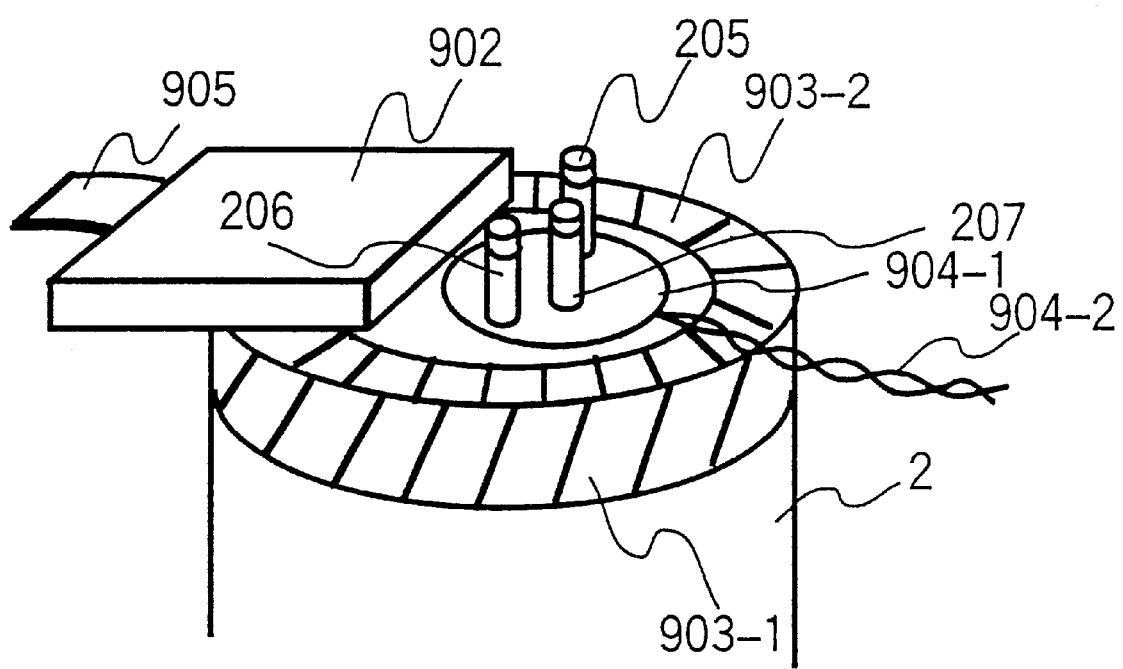
FIG. 8 is a perspective view illustrating an example of an upper portion of the cryostat of the biomagnetic field measurement apparatus according to the embodiment of the present invention.
Figure 9:
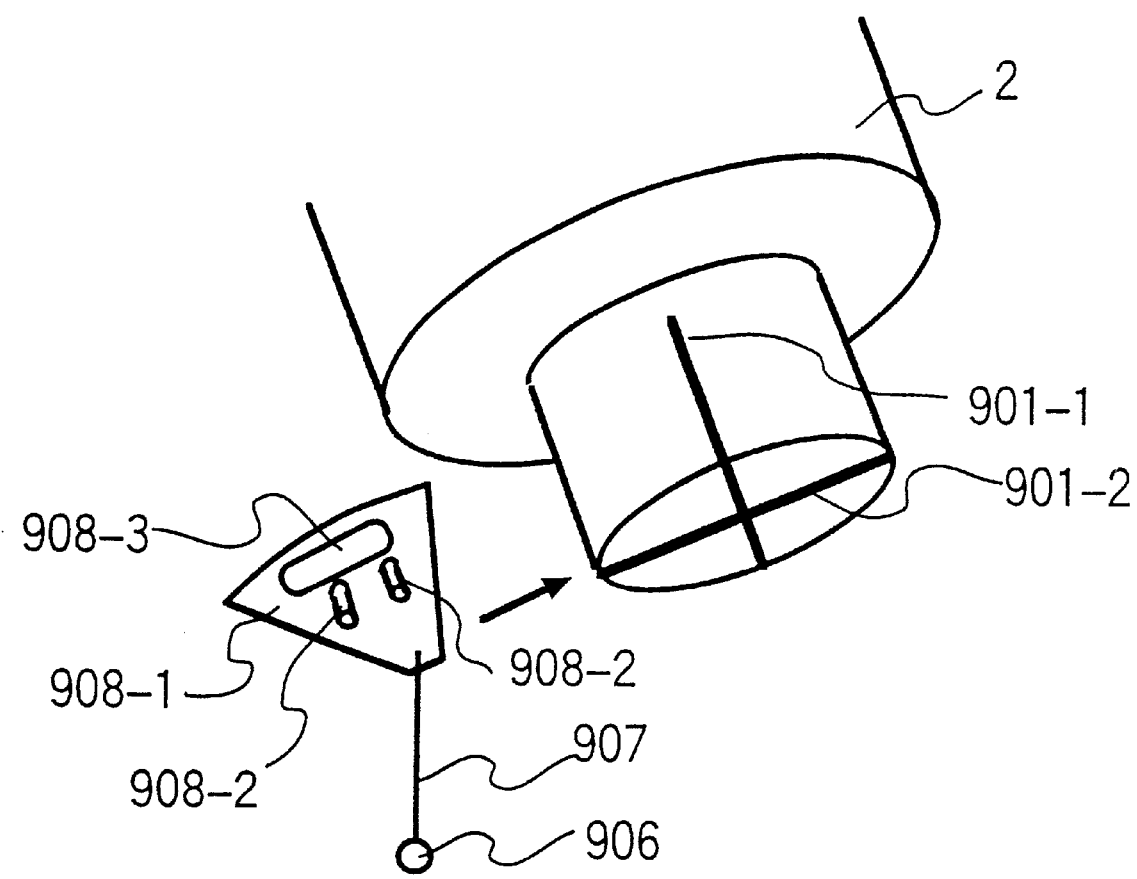
FIG. 9 is a perspective view illustrating an example of a lower portion of the cryostat of the biomagnetic field measurement apparatus according to the embodiment of the present invention.

FIG. 8 is a perspective view illustrating an example of an upper portion of the cryostat of the biomagnetic field measurement apparatus according to the embodiment of the present invention, and FIG. 9 is a perspective view showing an example of a lower portion of the cryostat of the biomagnetic field measurement apparatus according to the embodiment of the present invention.

As shown in FIG. 8, on the upper portion of the cryostat 2, there are disposed a cooling liquid introducing port 205 for introducing the liquid helium into the inside of the cryostat 2, an exhaust port 206 for exhausting helium gas evaporated from the inside of the cryostat 2 and a liquid level meter introducing port 207 for introducing the liquid level meter. Since the cold helium gas is exhausted from the exhaust port 206, vapor in the air becomes ice and drops of water and a moisture are produced on the upper surface of the cryostat 2. There is then the problem that, when the cryostat 2 is inclined, the bed, the subject to be inspected or the like are smudged by drops of water. To solve this problem, moisture-absorption sponges 903-1 (side surface sponge) and 903-2 (upper surface sponge) are respectively bonded to the outer peripheral side surface of the upper portion of the cryostat 2 and the upper surface of the cryostat 2, thereby resulting in moisture being absorbed and in the air seasoning of the cryostat 2.

Further, in order to dry moisture more reliably, a heater wire 904-1 (nichrome wire coated with vinyl) is bonded to the upper surface of the cryostat 2 by a high heat-conduction tape such as an aluminum tape, a current flows in a copper wire 904-2 connected to the heater wire 904-1 from a power supply of a thyristor control (temperature control) to heat the heater wire 904-1 portion, whereby the upper surface of the cryostat 2 is maintained at a temperature higher than a room temperature (or not less than 0° C.). When the magnetometer driving unit 4 is operated (i.e. state in which the biomagnetic field is measured), the power supply for supplying a current to the heater wire 904-1 is disconnected. It is preferable that the power supply may be automatically disconnected by automatically detecting the operation state of the magnetometer driving unit 4. That is, upon measurement in which magnetic fields are detected by operating the magnetometer driving unit 4, a current may be automatically prevented from flowing in the heater wire 904-1. Further, if there is generated a noise when the heater wire 904-1 or copper wire 904-2 induces electromagnetic waves, then the electrical connection of the heater wire 904-1 or the copper wire 904-2 may be disconnected by a suitable means such as a relay circuit in the inside or in the outside of the shielded room.

Further, on the upper portion of the cryostat 2, there are disposed a connector transforming box 902 for detecting a signal from a magnetometer disposed within the cryostat 2 and a connection cable 905 connected to the magnetometer driving unit 4 disposed in the outside of the shielded room 1.

Figure 10:
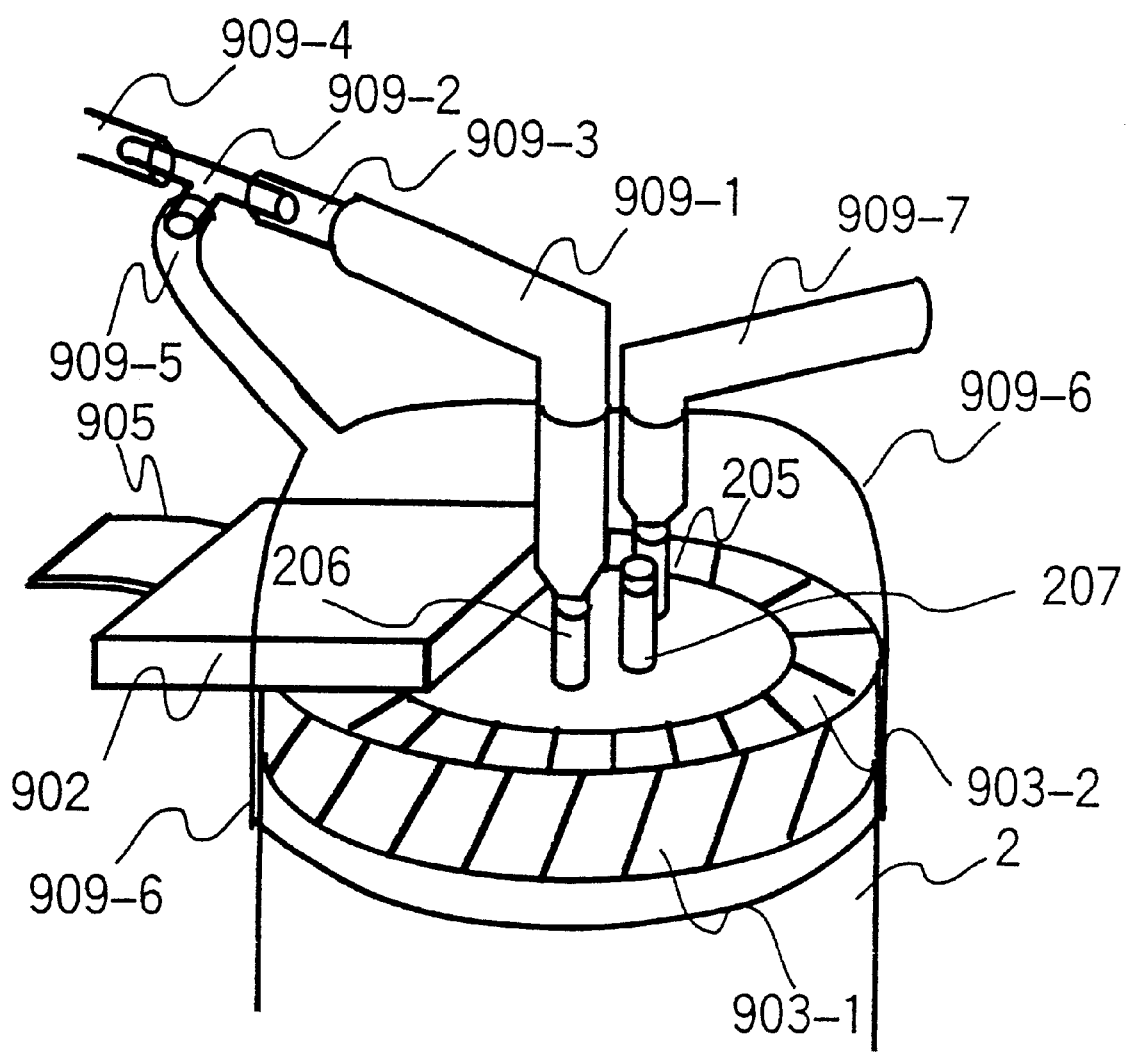
FIG. 10 is a perspective view illustrating another example of the upper portion of the cryostat of the biomagnetic field measurement apparatus according to the embodiment of the present invention.

FIG. 10 is a perspective view showing another example of the upper portion of the cryostat of the biomagnetic field measurement apparatus according to the embodiment of the present invention. FIG. 10 is a diagram used to explain another embodiment concerning the prevention of moisture shown in FIG. 8.

In the cryostat 2, there are disposed a transfer tube 909-7 comprised of an adiabatic double tube and which supplies liquid helium and connected to introducting port 205, and an exhaust gas port 909-1 connected to the gas exhaust port 206 and which is also comprised of the adiabatic double tube. An exhaust tube 909-3 is connected between the exhaust gas port 909-1 and a first end portion of an T-type branching tube 909-2. Further, the exhaust tube 909-4 for exhausting gas to the outside of the shielded room 1 and the second end portion of the T-type branching tube 909-2 are connected, and an exhaust tube 909-5 connected to a moisture preventing pack 909-6 and the third end portion of the T-type branching tube 909-2 are connected to branch the flow of helium gas into the exhaust tube 909-4 and the exhaust tube 909-5.

The whole of the upper portion of the cryostat 2 is covered with the moisture preventing pack 909-6 to thereby prevent helium gas from being leaked into the room. As a material for forming the moisture preventing pack 909-6, there is used a pack (bag) made of a polymer film having a small helium gas permeability. As the polymer film, for example, there is used a polyester material (e.g. PET (polyethylene terephthalate) which is difficult to be deformed even when a temperature is lowered upon introducing liquid helium. According to the above-mentioned arrangement, the upper portion of the cryostat 2 is filled with helium gas and the upper portion of the cryostat 2 is shielded from the vapor in the inside of the room so that moisture cain be prevented from being produced on the upper portion of t.he cryostat 2 so as not to produce a drop of water.

Further, when the exhaust tubes 909-3, 909-4, 909-5 and the T-type branching tube 909-2 are cooled so that a drop of water is produced from a moisture produced from the exhaust tubes themselves, such a moisture can be prevented from being produced by wrapping the adiabatic tube around the exhaust tubes 909-3, 909-4, 909-5 and the T-type branching tube 909-2.

The sponges 903-1, 903-2 shown in FIG. 8 may be disposed on the upper portion of the cryostat 2 and the whole of the upper portion of the cryostat 2 may be covered with the moisture preventing pack 909-6, whereby a drop of water can be prevented from being produced from moisture produced on the upper portion of the cryostat 2.

As shown in FIG. 9, as lines for easily detecting the rotation direction of the cryostat 2, there are displayed two display lines 901-1, 901-2 in the form of "+". Also, in order for the operator to position the center of the cryostat 2 and the measured place with ease, there is prepared a position fitting member 908-1 having a fan-like shape and which has a shape congruent to a part of the bottom surface of the cryostat 2. The position fitting member 908-1 hag attached thereto a support 908-2 for positioning the side surface of the cryostat in such a manner that a weight marker 9065 attached to a string 907 may be disposed at the center position of the bottom surface of the cryostat 2. Further, the position fitting member 908-1 has defined therein a horizontal hole 908-3 to enable the user to hold the cryostat 2 with ease.

Figure 11:
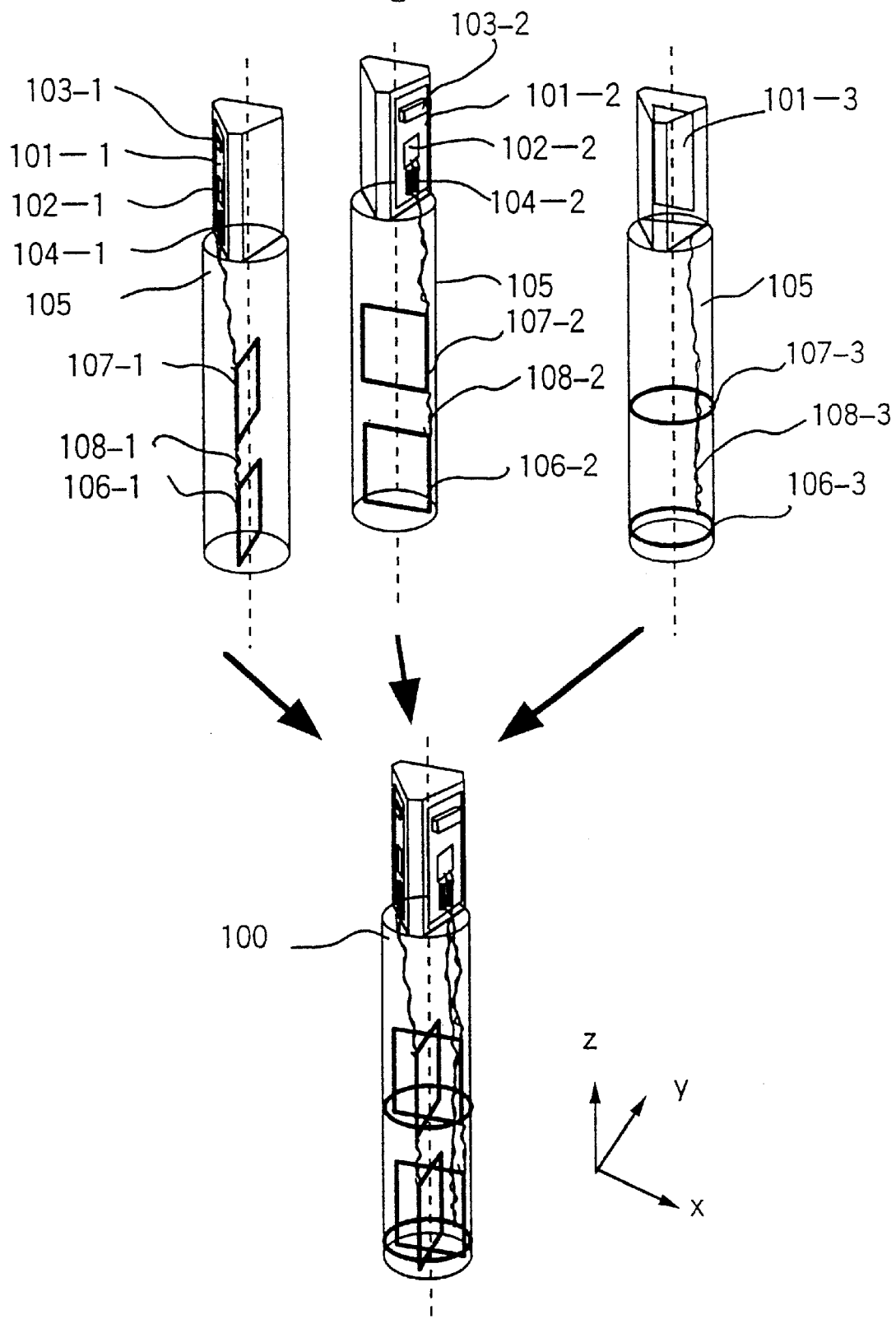
FIG. 11 is a perspective view illustrating an example of a magnetometer used in the biomagnetic field measurement apparatus according to the embodiment of the present invention.

Before elevating the bed 8, the operator determines the angle of the cryostat 2 and matches the cryostat 2 with the position of the measured subject to be inspected. Then, the operator elevates the bed 8 so that the center of the bottom surface of the cryostat can be rapidly positioned at the measured place. FIG. 11 is a perspective view illustrating an example of a vector magnetometer (one bobbin includes magnetometers for detecting magnetic field components or three directions of x, y, z) used in the biomagnetic field measurement apparatus according to the embodiment of the present invention. The upper portion of FIG. 11 independently shows detection coils for measuring magnetic field components ($B_x$, $B_y$, $B_z$ from left) of three directions of x, y, z. The lower portion of FIG. 11 shows the state in which detection coils of magnetic field components of three directions are formed on one bobbin 100.

A detection coil 106-1 and a compensation coil 107-1 are disposed in the direction in which the magnetic field component (B.) of x direction is detected. In order to reverse the detected magnetic field direction (e.g. $B_x$ and $-B_x$), a superconducting wire (e.g. Nb wire, Nb—Ti—Cu wire, etc.) is wrapped around the bobbin 100 in the opposite direction, thereby forming a first-order differential type gradiometer for canceling a uniform magnetic field. The detection coil 106-1 and the compensation coil 107-1 are electrically connected in series via a single superconducting wire. In order to prevent coils from being formed except the detection coil 106-1 and the compensation coil 107--i, portions other than the detection coil 106-1 and the compensation coil 107-1 are all twisted like a twist portion 108--i.

The superconducting wire which forms, the detection coil is superconducting-connected by a superconducting pad 104-1 (plate of niobium (Nb) and plumbum (Pb), etc.) and the superconducting pad 104-1 and the SQUID chip 101-1 are connected by superconducting bonding.

Figure 13:
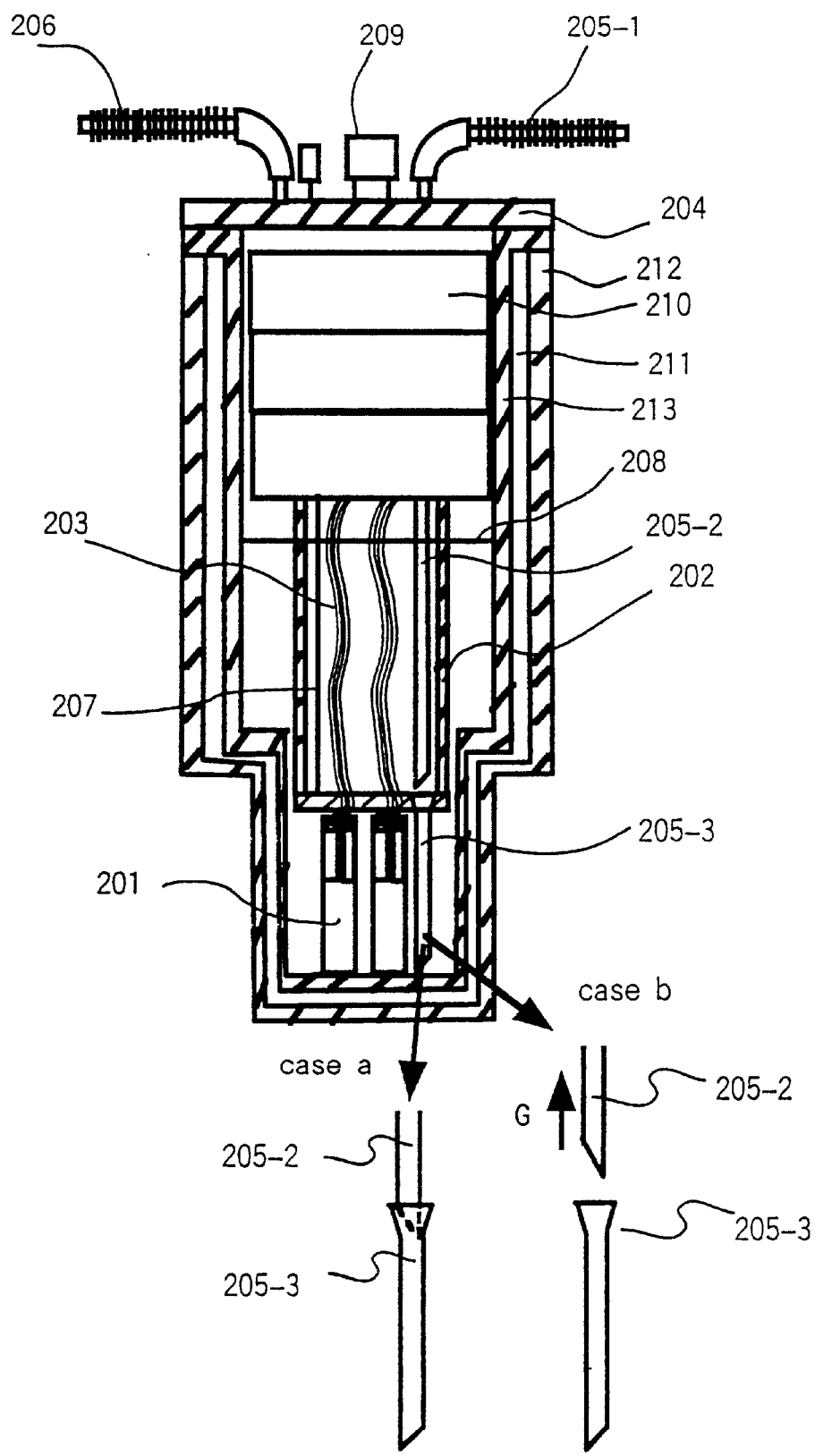
FIG. 13 is a cross-sectional view illustrating the inside of the cryostat used in the biomagnetic field measurement apparatus according to the embodiment of the present invention.

The SQUID chip 101-1 and a measurement circuit are connected through a connector 103-1 by a wiring 203 (see FIG. 13) in the inside of the cryostat 2. The layout of the magnetometers within the cryostat 2 will be described later on (FIGS. 12 and 13).

Similarly, a detection coil 106-2 and a compensation coil 107-2 are disposed in the direction in which the magnetic field component ($B_y$) of the y direction is detected. Also, in order to reverse the detected magnetic field direction, a superconducting wire (e.g. Nb wire, Nb—Ti—Cu wire, etc.) is wrapped around the bobbin 100, thereby forming a first-order differential gradiometer for canceling a uniform magnetic field being formed. The detection coil 106-2 and the compensation coil 107-2 are connected through the superconducting pad 104-2 to a SQUID chip 102-2. The output is connected to a normal temperature unit via the connector 103-2. The arrangement for detecting the magnetic field component ($B_z$) of the z direction also is similar, and therefore need not be described. A vector magnetometer for vector-measuring a magnetic field can be formed by forming the magnetometers for detecting the magnetic field components of the three directions in one bobbin 100.

Incidentally, the base line of the gradiometer is 60 mm, the diameter of the detection coil for detecting the magnetic field component of the z direction is equal to the bobbin diameter, i.e. 20 mm and the size of the detection coils for detecting the magnetic field components of the x and y directions is 20 mm×16 mm.

FIG. 12 is a perspective view showing an example in which the four magnetometers used in the biomagnetic field measurement apparatus according to the embodiment of the present invention are arranged, and illustrates an example of the arrangement of the four magnetometers in which the magnetometer shown in FIG. 11 is disposed in a 2×2 matrix fashion. The tip end portions of the four magnetometers are disposed at square-like lattice points spaced apart by 30 mm within the plane parallel to the xy plane. By the vector magnetometers formed on the respective bobbins 100-1, 100-2, 100-3, 100-4, the respective magnetic field components ($B_x$, $B_y$, $B_z$) are detected at four places, thereby resulting in magnetic field wave forms of 12 channels in total being obtained. Also, the arrangement of the magnetometers is not limited to 2×2 and may be either 3×3 to 8×8 or may be disposed in a circular fashion. Furthermore, 2×2 to 8×8 conventional magnetometers for measuring the magnetic field component ($B_z$) of the z direction may be disposed in either a matrix fashion or in a circular fashion.

FIG. 13 is a cross-sectional view showing an example of the arrangement of the inside of the cryostat used in the biomagnetic field measurement apparatus according to the embodiment of the present invention, and illustrates a cryostat in which the arrangement of the magnetometers shown in FIG. 12 is disposed. The cryostat 2 is comprised of an outer cylinder 212 and an inner cylinder 213 made of GFRP (glass fiber reinforced plastic). etc. In order to avoid heat from entering from the outside of the outer cylinder 212, a space between the inner cylinder 213 and the outer cylinder 212 is formed as a vacuum layer 211, and the inside of the vacuum layer 211 is covered with a radiation shield such as aluminum coated polyester film or the like and a thermal shield such as a copper (Cu) plate or the like.

In the inside of the inner cylinder 213 of the cryostat 2, there is stored a liquid helium 208. A bobbin 201 corresponding to the bobbins (100, 100-1, 100-2, 100-3, 100-4) shown in FIGS. 11, 12 is disposed at the bottom portion of the cryostat 2. In order to integrally form the bobbin 201 with a flange 204, the bobbin 201 is attached through an adiabatic member 210 to the lower portion of a magnetometer holding portion 202 by the magnetometer holding portion 202. The bobbin 201 is interconnected up to a connector portion 209 (902 in FIG. 8) via a high electric resistance wire such as manganin and a low heat invasion wire so that it may be electrically connected to a measuring circuit of a normal temperature portion. Also, to introduce the liquid helium into the cryostat 2, there are disposed a transfer tube main body 205-1 having a double wall structure, an introducing portion 205-2 integrated with the main body 205-1 and a connection tube 205-3.

When there exists no liquid helium in the inside of the cryostat 2, as shown by a case a, the liquid helium introduced from the transfer tube main body 205-1 is introduced by connecting the introducing portion 205-2 and the connection tube 205-3 having a funnel structure and can be cooled from the lowermost bottom portion of the inside of the cryostat 2. When the liquid helium is supplemented under the condition that the liquid helium still remains in the inside of the cryostat 2, as shown by a case b, in order that the introducing portion 205-2 and the connection tube 205-3 may be detached from each other, the transfer tube main body 205-1 is elevated by several centimeters in the arrow G direction. According to this arrangement, when the liquid helium is introduced from the transfer tube main body 205-1, helium gas having a temperature considerably higher than 4.2 K obtained immediately after the transfer can be prevented from being directly sealed into the liquid helium that still remains in the inside of the cryostat 2. Thus, when the liquid helium is filled, the loss of the liquid helium can be decreased.

Also, in the flange portion 204, there are disposed a level meter 207 for monitoring a remaining quantity of the liquid helium and a gas exhaust port 206. The gas exhaust port 206 may be comprised of a double tube having a vacuum layer so that a drop of water can be prevented from being produced on the outside of the gas exhaust port 206.

While the present invention has a premise such that the liquid helium is stored as described above, the present invention is not limited thereto, when a refrigerating machine is used, the inner cylinder 213 is not needed. When the high-temperature superconducting SQUID is used, a stored refrigerant may be liquid nitrogen.

Figure 14:
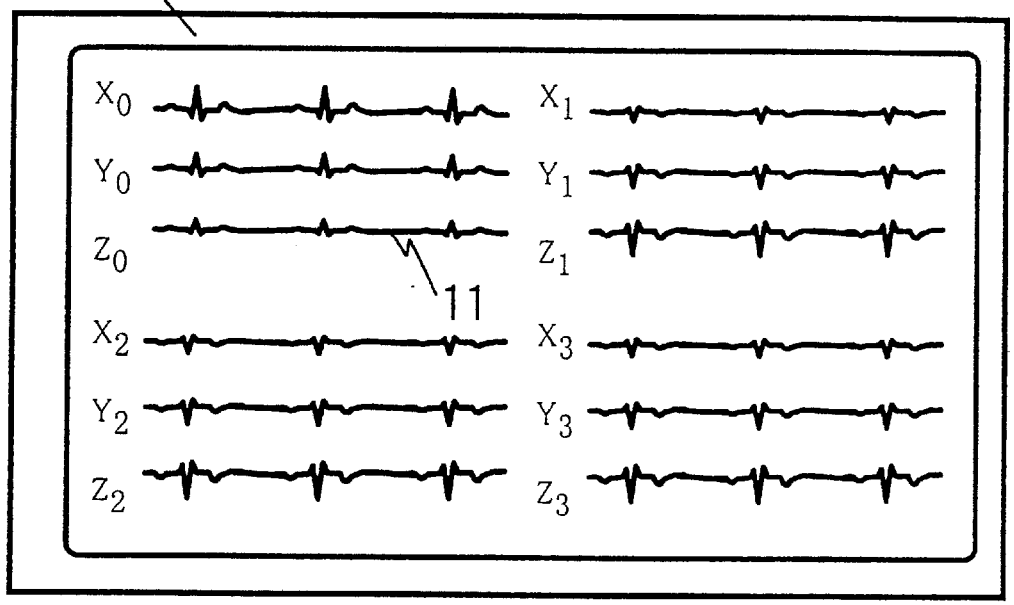
FIGS. 14 and 15 are diagrams showing examples of picture screens for displaying the magnetic field wave forms in the biomagnetic field measurement apparatus according to the embodiment of the present invention.
Figure 15:
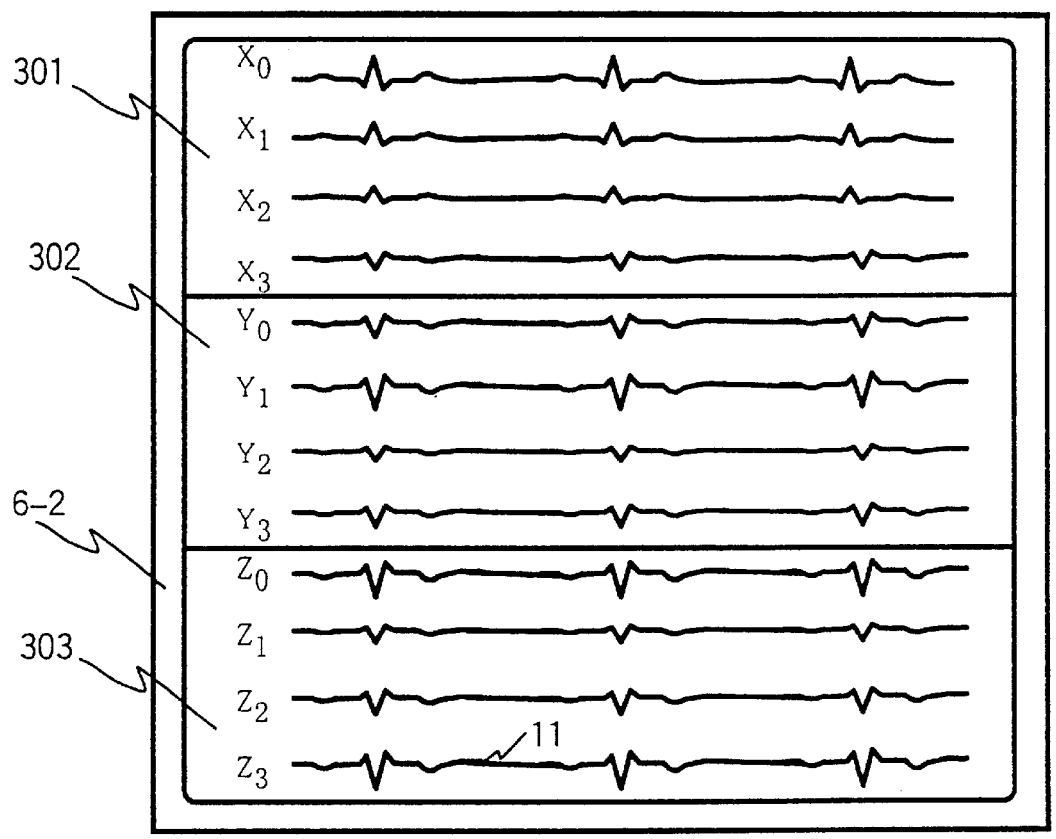

FIGS. 14, 15 are diagrams showing examples of picture screens for displaying magnetic field wave forms in the biomagnetic field measurement apparatus according to the embodiment of the present invention, and illustrate examples of displayed pictures of the magnetic field wave forms 11 obtained from the arrangement of the magnetometers shown in FIG. 12. On the display screen 6-1 shown in FIG. 14, there are displayed a wave form of a magnetic field component ($B_x$) of the x direction, a wave form of a magnetic field component ($B_y$) of the y direction and a wave form of a magnetic field component ($B_z$) of the z direction at every vector magnetometer (magnetic wave forms 11 of $B_x$, $B_y$, $B_z$ obtained by the vector magnetometers formed on the ith (i=0, 1, 2, 3) are respectively shown by $z_i$, $y_i$, $z_i$).

In the display screen 6 shown in FIG,. 1 and the display screen 6-2 shown in FIG. 15, the magnetic field wave form 11 is classified into the wave form of the magnetic field component ($B_x$) of the x direction, the wave form of the magnetic field component ($B_y$) of the y direction and the wave form of the magnetic field component ($B_z$) of the z direction, and are separately displayed on regions 301, 302, 303. In the region 301, there is displayed a magnetic. field wave form $x_i$ (i=0, 1, 2, 3) of $B_x$ obtained by the vector magnetometer formed on the ith (i=0, 1, 2, 3) bobbin. In a like manner, in the regions 302, 303, there are displayed a magnetic field wave form $y_i$ (i=0, 1, 2, 3) of $B_y$ and a magnetic field wave form $z_i$ (i=0, 1, 2, 3) of $B_z$.

When the magnetic field distribution is displayed, there is obtained a magnetic field distribution map based on the magnetic field component ($B_y$) of the y direction and the magnetic field component ($B_z$) of the z direction by using any of $B_x$, $B_{xy}$ (equation (1)) and $B_{xyz}$ (equation (2)).

$$B_{xy} = \sqrt{(B_x^2 + B_y^2)} \quad (1)$$

$$Bxyz = \sqrt{(B_x^2 + B_y^2 + B_z^2)} \quad (2)$$

When an optimum place in which a magnitude of a magnetic field is large is searched prior to the measurement of the biomagnetic field, it is recommended to search the maximum value of the magnetic field distribution of $B_{xyz}$. magnetic field distribution maps $B_z$, $B_{xy}$ (equation (1)), $B_{xyz}$ (equation (2)) can be displayed together with the displayed pictures shown in FIGS. 1, 14, 15, 16 simultaneously.

FIG. 16 is a diagram showing an example of a picture screen for displaying the position of the fetus in the biomagnetic field measurement apparatus according to the embodiment of the present invention, and illustrates a projection picture 12 onto the x-y plane of the position of the estimated heart shown in FIG. 1 and a projection picture 13 onto the x-z plane or the y-z plane of the position of the estimated heart.

In the projection picture 12, a projection display picture 405 is displayed on the upper left, and a projection position 16-1 of the heart of the fetus is displayed by open circles (①) to ⑧). Numerals within the open circles represent the order of heart beats. A dotted line 401 (y axis) and a dotted line 402 (x axis) are display lines for displaying the position (① in the example of FIG. 16) of the heart at a time point of the display line 503 shown on the magnetic field wave form 11 more clearly. The dotted line 401 are continuously displayed on the projection picture 13 so that the operator may clearly understand the three-dimensional position of the heart of the foetus.

In the projection picture 13, a projection display picture 406 is displayed on the upper left, the magnetometer projection position 15-2 is represented by a square, and the position 404 (or the position right overhead the bottom surface of the cryostat 2) of the surface of the abdomen of the mother's body is represented by a straight line. In the projection picture 13, similarly to the projection picture 12, the position of the heart at the time point of the display line 503 shown in the magnetic field wave form 11 in FIG. 1 is illustrated by a dotted line 401 (y axis) and a dotted line 403 (x axis) more clearly. A display 407 of number showing movements of the foetus in the projection pictures 12, 13 represents the movements of the position of the heart of the foetus in the form of numerals.

$V_z$ represents an average speed of the z direction, $V_{xy}$ represents an average speed within the x-y plane, and $V_t$ is defined by the equation (3) and which expresses the average value of $V_z$ and $V_{xy}$ (unit: mm/sec). The average speed can be calculated by averaging a value, which results from a movement distance of every heart beat by a time of heart beat interval, with all heart beats within the measurement time.

$C_z$ is a movement distance of the z direction within the measurement time, $C_{xy}$ is a movement distance on the xy plane within the measurement time, and $C_t$ is defined by the equation (4) and which expresses the average value of $C_z$ and $C_{xy}$ (unit: mm). The movement distance can be calculated by adding the movement distance of each heart beat within the measurement time.

$R_{xy}$ represents a total rotation amount in the direction of the estimated dipole. The rotation amount can be calculated by computing a difference amount $\theta_n$ between an angle $\theta_N$ in the direction (orientation) of the dipole estimated at Nth heart beat and an angle $\theta_{N+1}$ of the orientation of the dipole estimated at (N+1)th heart beat according to the equation (5) or by computing an added value $\Sigma\theta_n$ (n=1, . . . , M) within a measurement time (1 to M heart beats) or the added value $\Sigma|\theta_n|$ (n=1, . . . , M) of the absolute value. Here, the reason that the parameter indicative of the rotation amount of the z direction is not displayed is that the position and the magnitude of the dipole can be estimated only in the current direction within the plane (i.e. x-y plane) parallel to the surface (position 404 of the surface of the abdomen of mother's body in FIG. 16) of the measured member. Thus, the rotation amount only in the x-y plane is illustrated.

$$V_t = (\sqrt{V_z^2 + V_{xy}^2}) \quad (3)$$

$$C_t = (\sqrt{C_z^2 + C_{xy}^2}) \quad (4)$$

$$\theta_n = (\theta_{N+1} - \theta_N) \quad (5)$$

By representing the movements of the position of the heart of the foetus as a numeral, the movements of the position of the heart of the fetus also can be visually confirmed. In addition, by the magnitude (absolute value of dipole which will be described later on) of the dipole, the projection positions 16-1, 16-2 of the heart of the fetus shown by open circles in FIG. 16 can be displayed while colors are changed depending on the magnitudes of the dipole (e.g. red represents the dipole magnitude larger than 200 nA·m, blue represents the dipole magnitude less than 100 nA·m and yellow represents other cases). When the change of color is given to the display of the projection positions 16-1, 16-2 of the heart of the fetus, in a case of a disease such as arrhythmia, the heart beat in which arrhythmia occurs is displayed in red and can be displayed more clearly.

Further, instead of the open circles representing the projection positions 16-1, 16-2 of the heart of the foetus in FIG. 16, the magnitude and the orientation of the dipole can be represented by lengths and directions of arrows. If the magnitude and the direction of the dipole are expressed by the lengths and the directions of the arrows onto the projection positions 16-1, 16-2 of the heart of the fetus, it is possible to easily understand the existence of the rotation of the body of the foetus.

Figure 17:
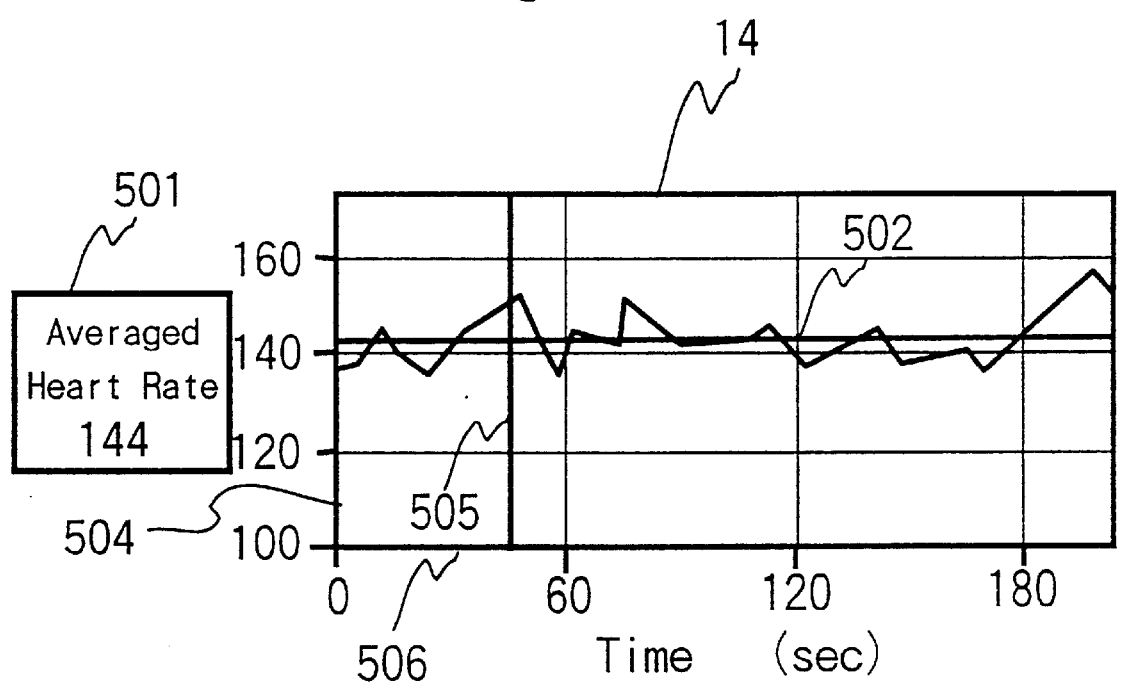
FIG. 17 is a diagram showing an example of a picture screen for displaying a heart rate of a fetus in the biomagnetic field measurement apparatus according to the embodiment of the present invention.
Figure 18:
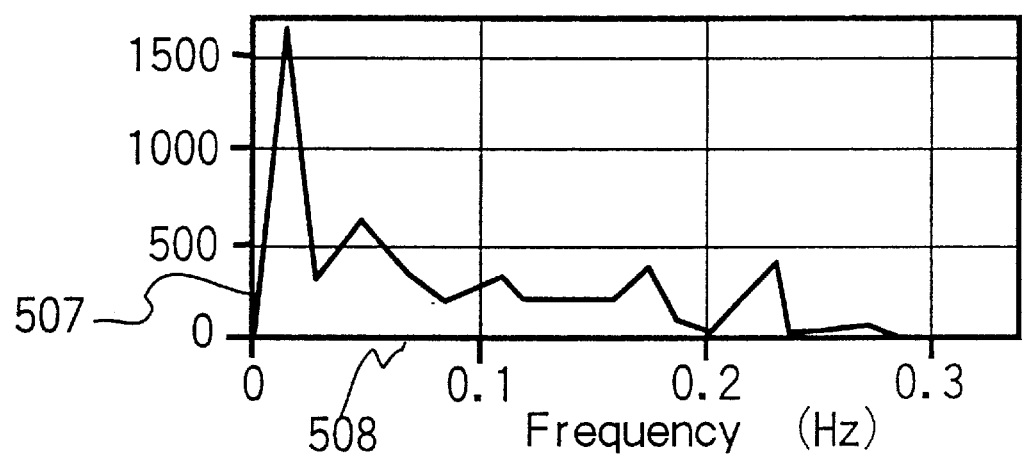
FIG. 18 is a diagram showing an example of a picture screen for displaying results obtained when the heart rate of the fetus is analyzed by FFT in the biomagnetic field measurement apparatus according to the embodiment of the present invention.

FIG. 17 is a diagram showing an example of a picture for displaying the heart rate of the fetus in the biomagnetic field measurement apparatus according to the embodiment of the present invention. FIG. 18 is a diagram showing an example of a picture for displaying results obtained when the heart rate of the fetus is FFT-analyzed in the biomagnetic field measurement apparatus according to the embodiment of the present invention. FIG. 17 shows a plot picture 14 of the heart rate variation of the foetus shown in FIG. 1. In the plot picture 14, a vertical axis 504 represents a heart rate, and a horizontal axis 506 represents a time.

A peak of R-wave is detected from a magnetic field wave form of a desired measured channel, an R-R interval ($T_1$ (sec)) of every heart beat is calculated, and the heart rate is obtained by computing $60/T_1$. In the side. of the plot picture 14, there is displayed an average heart rate (the average heart rate is 144 in the example of FIG. 17) within the measurement time of the magnetic field. In the plot picture 14, the average heart rate 501 is expressed by an average straight line 502. The display line 505 shows a position corresponding to a time point of the time display line 503 of the magnetic field wave form 11 shown in FIG. 1.

FIG. 18 shows results obtained when the wave form of FIG. 17 is FFT (Fast Fourier transform)-transformed, and illustrates the results on the display screen of the computer 6. A vertical axis 507 represents the power value, and a horizontal axis 508 represents the frequency. When the power spectrum is calculated, a time width for calculating the power spectrum can be freely varied within the measurement time of the magnetic field.

While the case in which the heart rate is used as described above, the plot picture 14 may be executed by using the R-R interval ($T_1$ (sec)) instead of the heart rate. Also, the power spectrum can be calculated by FFT-transforming the R-R interval ($T_1$ (sec)).

Figure 19:
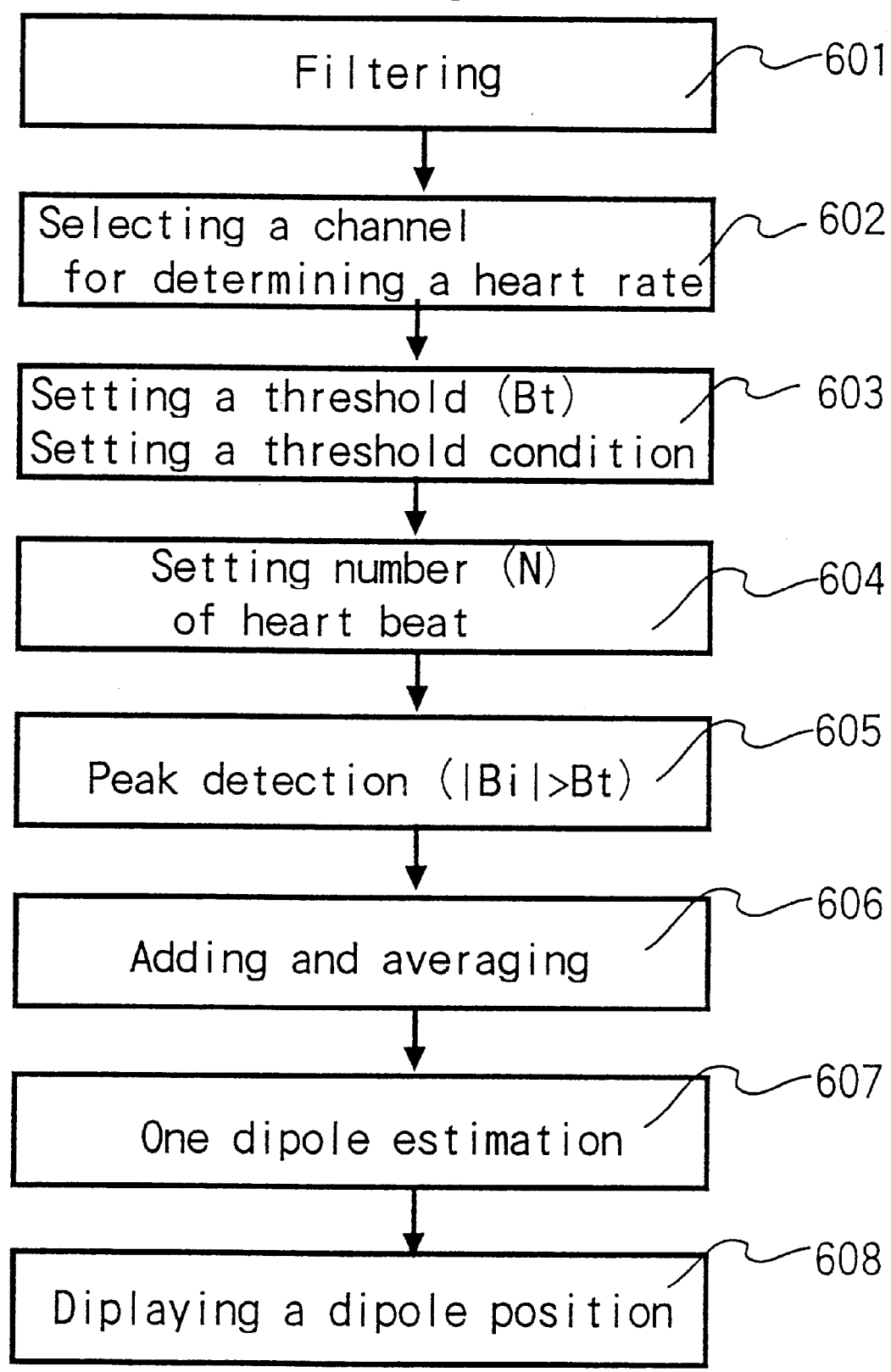
FIG. 19 is a block diagram showing a flow of a data processing executed until a dipole is displayed on the screen.

FIG. 19 is a block diagram showing a flow of data processing executed until the position of the dipole is displayed on the screen. A filter processing 601 for eliminating a noise having a frequency less than or equal to 5 Hz to 6 Hz (e.g. 1 Hz, 2 Hz, 3 Hz) generated in accordance with a respiration of a mother's body is effected on the measured magnetic field signal. The filter processing 601 (process 1) executes a high-pass filter processing by a digital filter. In addition to the high-pass filter processing, there may be executed a notch filter processing for eliminating a noise such as 50 Hz of a power supply noise and high-frequency components 100 Hz, 150 Hz of a power supply noise.

Then, in order to detect a heart rate, there is selected an optimum channel having an excellent S/N (heart rate detection channel selection 602 (process 2)). As shown in FIG. 1, an operator selects a channel by clicking a bottom (in the example of FIG. 1, the button 17-1 is selected). Then, a threshold value ($B_t$: e.g. B=2 pT) for detecting a heart rate is set while monitoring the magnetic field wave form thus measured (threshold value setting and threshold value condition setting 603 (process 3)). After the threshold value is set, there should be set threshold value conditions such as detecting the magnetic field wave forms at a cross point at which the heart rate and the threshold value cross each other, or detecting the magnetic field wave form at a maximum value which exceeds a threshold value larger than the threshold value, or detecting the magnetic field wave form at a minimum value which is smaller than the threshold value, if necessary.

Then, when the measured magnetic field wave form has a poor S/N, a number (N) of heart beat for adding and averaging is set (standard value is N=1 without addition) (setting number of heart beat for adding and averaging 604 (process 4)). Then, by using a magnetic field ($B_i$) of a channel i for detecting a heart beat, a time point at which $|B_i|>B_t$ (or $B_i>B_t$, $B_i<B_t$) is established is detected in accordance with the above-mentioned threshold condition setting, and is peak-detected (peak detection 605 (process 5)). Then, using the peak-detected time point as a synchronizing signal, magnetic field signals of all channels are added and averaged by a duration (setting of duration can be varied) of 100 ms around the peak-detected time point or only by an intensity of the magnetic field of the peak-detected time point (adding and averaging process 606 (process 6)).

When N=3, for example, is set, a wave form which results from adding and averaging first, second and third heart beats is substituted for a wave form of a first: heart beat. A wave form of kth heart beat will be set to a wave form which results from adding and averaging kth heart beat, (k+1)th heart beat and (k+2)th heart beat, sequentially. Based on the results obtained by adding averaging heart beats, an estimation 607 (process 7) of one dipole is estimated from a magnetic field distribution of all channels of the peak-detected time point (i.e. let it be assumed that only one dipole exists in the heart of a foetus). A practical method for estimating the position and magnitude of the dipole will be described later on. The dipole thus obtained from the above-mentioned results is displayed by a dipole picture display 608 (process 8) in accordance with the method described with respect to FIGS. 1 and 16. Also, the variation of the heart beat can be displayed based on the peak-detected time point as shown in FIG. 17.

Three methods of estimating the position and magnitude of the dipole will be described hereinafter. In the following description, <physical amount> indicates that a physical amount is a vector.

(First Method)
Method Using a Method of Least Square Which is a Method of Estimating the Position and Magnitude of the Dipole According to the Prior Art Assuming that only one dipole exists in the heart of the foetus (assuming that coordinates of the dipole are ($x_i$, $y_i$, $z_i$), then a magnetic field vector $B_s$ made by a dipole placed at the coordinates ($x_i$, $y_i$, $z_i$) and which has an intensity ($Q_x$, $Q_y$, $Q_z$) is calculated by an analytic solution considering a return current (feedback current) analytically obtained by Sarvas (Phys. Med. Biol., Vol. 32, No. 1, pp. 11–22, 1987) or Biot-Savart equation. Then, a dipole <Q> placed at the tip end of the position vector <r> is calculated in such a manner that a square error ($E=\Sigma\{(B_i-B_s)^2\}$) (addition $\Sigma$ is executed over the number of measurement points) may be minimized. In order that the square error E may be converged rapidly, the coordinates of the heart of the foetus calculated by the ultrasonic diagnosis apparatus should preferably be used as the initial value of the coordinates of the dipole.

Figure 20:
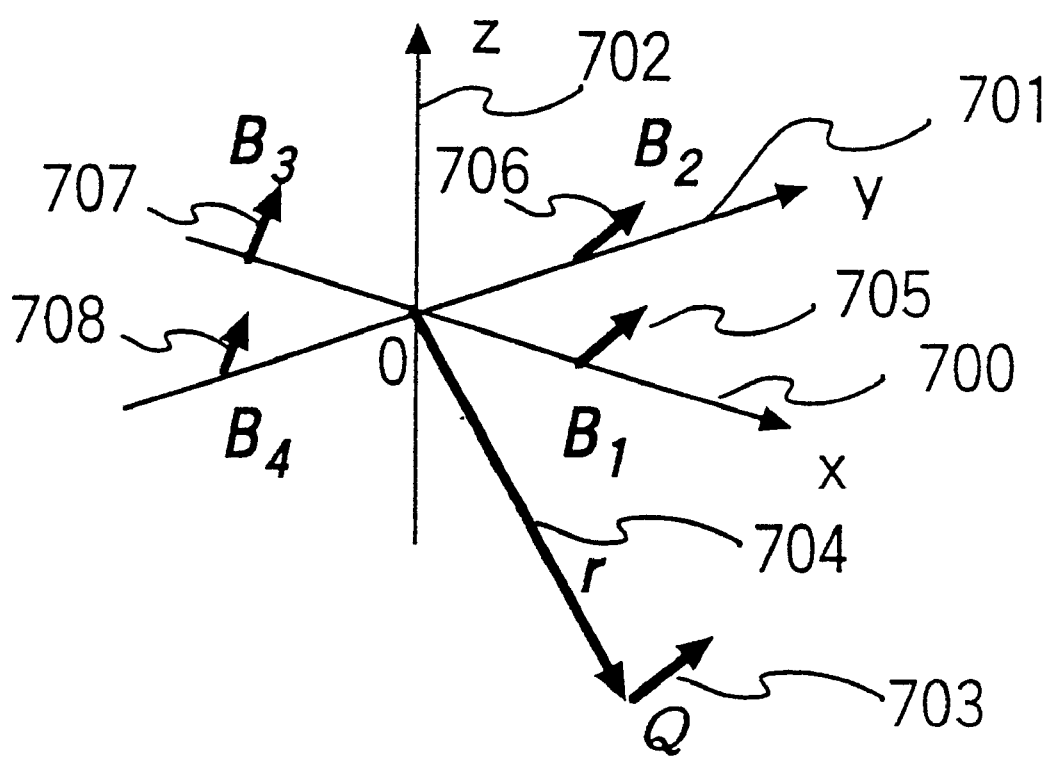
FIGS. 20 and 21 are diagrams used to explain a method of estimating the position and the magnitude of the dipole in the embodiment of the present invention.
Figure 21:
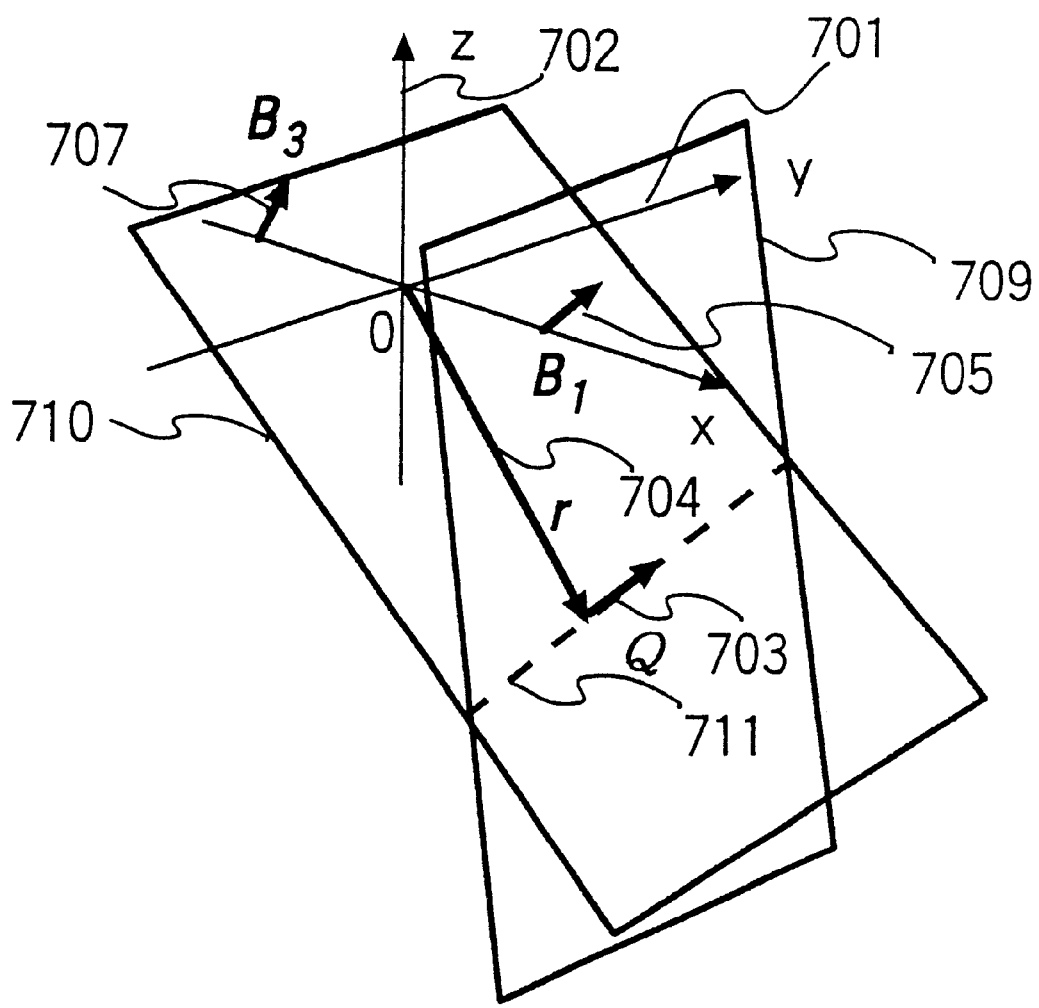

(Second Method)
Method of Estimating the Position and Magnitude of the Dipole at High Speed FIGS. 20 and 21 are diagrams used to explain the method of estimating the position and magnitude of the dipole. Similarly to the above-mentioned first method, let it be assumed that only one dipole exists in the heart of the fetus. As a result of measuring magnetic field vectors by using the array of the 2×2 vector magnetometers shown in FIG. 12, as R waves of heat electric power of the fetus, let it be assumed that measured magnetic field vectors <$B_1$> (705), <$B_2$> (706), <$B_3$> (707), <$B_4$> (708) (shown by $B_1$, $B_2$, $B_3$, $B_4$ in FIG. 20) are measured. As shown in FIG. 20, x coordinate 700 is assumed to be a straight line passing magnetic field vectors <$B_1$> (705) and <$B_3$> (707), y coordinate 701 is assumed to be a straight line passing magnetic field vectors <$B_2$> (706) and <$B_4$> (708), and z coordinate 702 is assumed to be a straight line passing an intersection O between the x coordinate 700 and the y coordinate 701 and which is perpendicular to the x coordinate 700 and the y coordinate 701. The dipole <Q> (703) is placed at the tip end of the position vector <r> (704). The position and the magnitude of the dipole are estimated by using the position vector <r> (704) and the dipole <Q> (703).

Initially, as shown in FIG. 21, let us assumed a plane 710 perpendicular to the magnetic field vector <$B_3$> (707) and a plane 709 perpendicular to the magnetic field vector <$B_1$> (705). The dipole <Q> (703) is placed on the two perpendicular planes 710 and 709 and placed on a straight line 711 shown by a dotted line in which the two perpendicular plane 709 and 710 cross each other. The position vector 704 <r> is assumed to be an equation (6). In the equation (6), $\alpha$ represents an arbitrary value, and <v> is expressed by an equation (7) and <$\omega$> is expressed by an equation (8). <$e_x$> represents a unit vector in the x direction, a represents et value of X coordinate at the position of the detection coil for detecting the magnetic field <$B_1$> (705), and $\beta$ is expressed by an equation (9). In the equations (7) to (9), symbol "x" represents a vector product, and symbol "." represents a scalar product.

$$<r>=<v>+\alpha<\omega> \quad (6)$$

$$<v>=\beta<B_1>\times<\omega>+a<e_x> \quad (7)$$

$$<\omega>=<B_1>\times<B_3>/(|<B_1>\times<B_3>|) \quad (8)$$

$$\beta=-2a<B_3>\cdot<e_x>/(<B_3>\cdot(<B_1>\times<\omega>)) \quad (9)$$

From the equations (6) to (9), an equation of straight line 711 is obtained. Then, while sequentially changing the value (e.g. −0.01 m to 0.01 m) of $\alpha$ of the equation (6) and the value of the dipole <Q> (703), magnetic field vectors of the respective measurement points are calculated by using the Biot-Savart equation or the equation of the above-mentioned analytical solution obtained by the Sarvas. Then, the dipole <Q> (703) and the position vector <r> (704) are calculated in such a manner that a square error of a difference between the calculated magnetic field vectors and measured magnetic field vectors <$B_1$> (705), <$B_2$> (706), <$B_3$> (707), <$B_4$> (708) (shown by $B_1$, $B_2$, $B_3$, $B_4$ in FIG. 20) may be minimized. According to the above-mentioned arrangement, it is possible to estimate the position of the heart of the fetus and the intensity of the dipole. The application of the method of estimating the position and magnitude of the dipole using the equations (6) to (9) will be described below. With respect to R-wave of the electromotive force of the heart of the fetus, there is calculated a solution 1 of the equation (6). Then, with respect to S-wave or T-wave or near the S-wave, a solution 2 of the equation (6) is calculated by using the equations (6) to (9). An intersection (point at which two straight lines are most close to each other when there is no intersection) is calculated from the equations of the two straight lines of the solutions 1 and 2, and then the position vector <r> (704) can be obtained. Then, the dipole <Q> (703) is located at the position of the position vector <r> (704) in the direction of the straight line equation obtained from the solution 1 and magnetic field vectors of the respective measurement points are calculated by using the analytical solution obtained by the Sarvas (Phys. Med. Biol., Vol. 32, No. 1, pp. 11–22, 1987) or the Biot-Savart equation. Then, the magnitude of the dipole <Q> (703) is calculated in such a manner that a square error of a difference between the above magnetic field vectors and the measured magnetic field vectors <$B_1$> (705), <$B_2$> (706), <$B_3$> (707), <$B_4$> (708) (shown by $B_1$, $B_2$, $B_3$, $B_4$ in FIG. 20) may be minimized.

(Third Method)
Method of Approximately Estimating the Position and Magnitude of the Dipole The third method is a modified example of the first method. Assuming that only one dipole exists, then using a half infinite conductor model, the magnitude and the position of the dipole are estimated according to the least square method. The R-wave signal thus added and averaged from the heart of the foetus calculates $B_{xyz,i}$ (i=1~4) at every four magnetometers, the positions of the x direction and the y direction in which the ith magnetometer for applying the maximum value of $B_{xyz,i}$ (i=1~4) are set to the initial values ($x_i$, $y_i$) at the positions of the x direction and the y direction in which the dipole exists. Then, considering the thickness (12 mm in this embodiment) of the bottom surface of the cryostat as the initial value of the distance from the tip end of the ith magnetometer for applying the initial value ($z_i$) of the position in the z direction in which the dipole exists, i.e. the maximum value of $B_{xyz,i}$ (i=1~4) to the foetus of the mother's body, there is set a constant value between 50 mm and 60 mm, for example. Also, when the magnetic fields thus measured are $B_1$, $B_2$, $B_3$, $B_4$ (FIG. 20), art average value of six vector products ($B_1 \times B_2$, $B_1 \times B_3$, $B_1 \times B_4$, $B_2 \times B_3$, $B_2 \times B_4$, $B_3 \times B_4$) is obtained and set to the initial value ($Q_x$, $Q_y$) of the magnitudes of the x direction and the y direction of the dipole. An initial value ($Q_z$) of the magnitude in the z direction of the dipole is set to zero (0). A magnetic field $B_s$ vector formed by the dipole of the initial value ($Q_x$, $Q_y$, $Q_z$) of which the tip end exists at the initial value ($x_i$, $y_i$, $z_i$) of the <r> position vector thus set is calculated by the Biot-Savart equation or by the analytical equation obtained by Sarvas, and an absolute value of the dipole <Q> existing at the tip end of the position vector <r> is obtained by changing the initial value ($x_i$, $y_i$, $z_i$) and ($Q_x$, $Q_y$, $Q_z$) such that a least square error ($E=\Sigma\{(B_i-B_s)^2\}$) (addition $\Sigma$ is carried out over the number of measurement points) of the measured magnetic field vector $B_i$ (i=1~4) may be minimized. According to this method, although the direction of the dipole cannot be estimated accurately due to the existence of a volume current and a distribution current, this method is a method which is sufficient for simply estimating the orientation of the dipole.

The description has been made on various kinds of methods for estimating the position and the magnitude of the dipole when the measurement values of the magnetic fields using the arrangement of the vector magnetometers of FIG. 12 are used.

An example in which the position and the magnitude of the dipole are estimated by using the magnetic field component of the normal direction according to the prior art will be described below. In the following description, similarly to the first method, the second method and the third method, let us assume that only one dipole exists in the heart of the fetus.

Figure 22:
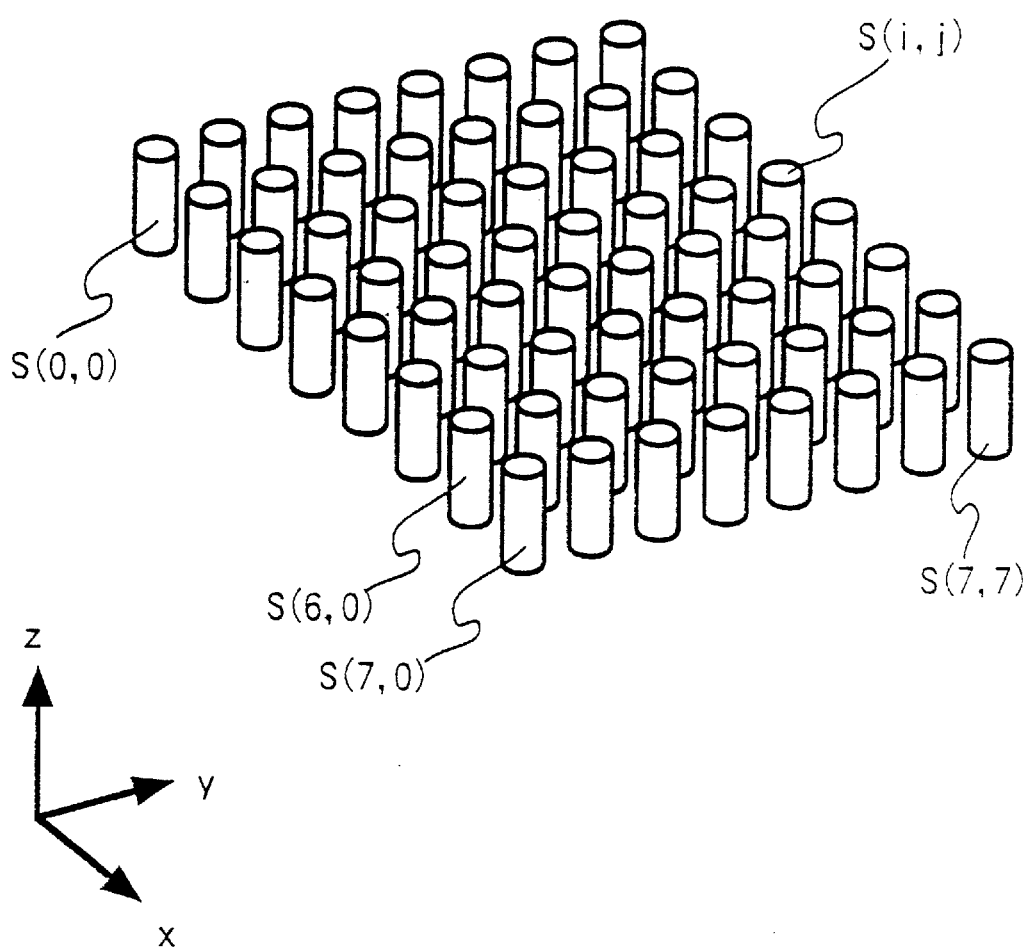
FIG. 22 is a perspective view illustrating an example of a manner in which magnetometers are arranged in a biomagnetic field measurement apparatus according to the prior art.

FIG. 22 is a perspective view illustrating an example in which magnetometers for measuring the magnetic field component in the normal direction are arranged in the prior-art biomagnetic field measurement apparatus. Magnetometers S (i, j) are disposed in a 8×8 matrix fashion which are spaced apart by 25 mm.

Figure 23:
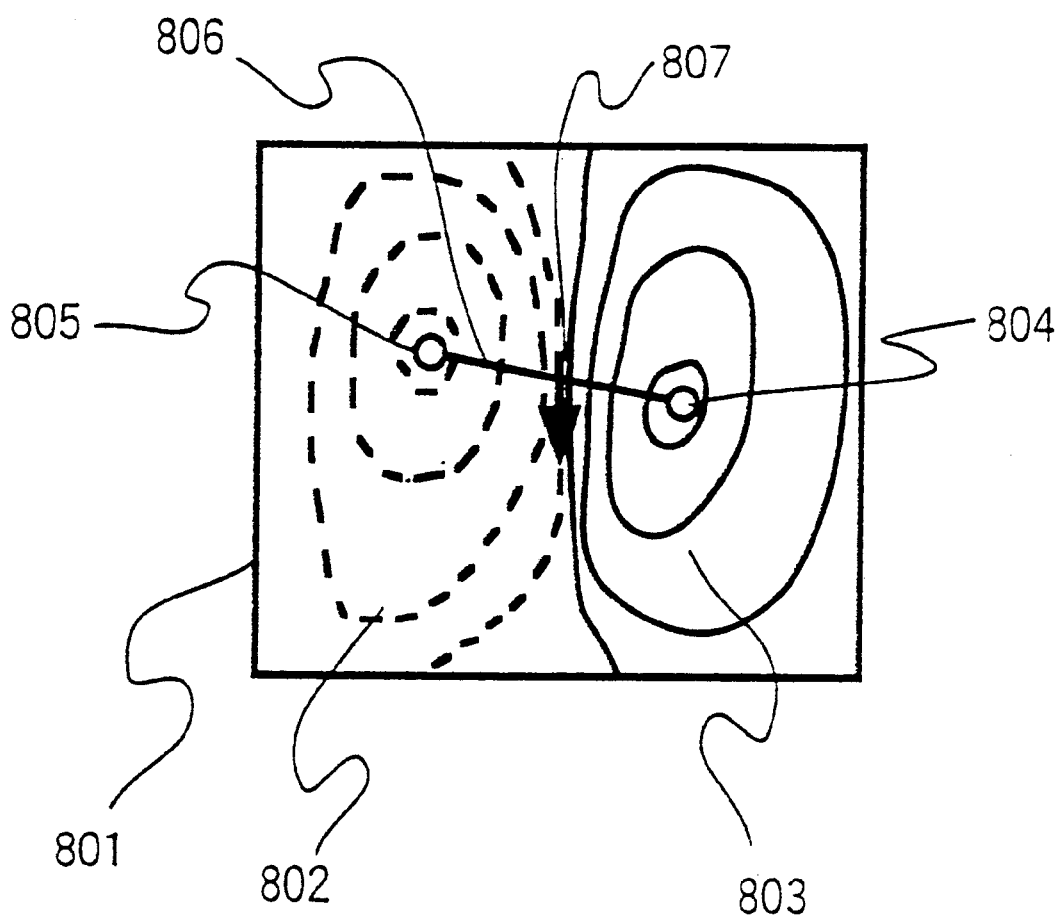
FIG. 23 is a diagram showing an example of a magnetic field distribution measured by the arrangement of the magnetometers in the biomagnetic field measurement apparatus according to the prior art.

FIG. 23 is a diagram showing an example of a distribution of magnetic fields measured by the arrangement of the prior-art biomagnetic field measurement apparatus, and illustrates a contour map (magnetic field distribution) 801 obtained by measuring the magnetic field of the foetus by using the arrangement of the magnetometers in FIG. 22.

In FIG. 23, a solid line shows a magnetic field 803 of the positive direction, and a dotted line shows a magnetic field 802 of the negative direction. L assumes a straight line distance 806 between a peak point 804 of the positive direction magnetic field 803 and a peak point 805 of the negative direction magnetic field 802. At that time, a dipole 807 exists at an intermediate L/2 point. The dipole 807 is a dipole perpendicular to the straight line 806 and has a left-hand direction orientation from the positive direction magnetic field 803 to the negative direction magnetic field 805. There is known a relation between a depth d in which the dipole exists and an intensity Q of the dipole (Journal of Magnetism and Magnetic Materials, 22, pp. 154–157 (1981)).

Since the magnetic field component in the normal direction is measured, a relation between the straight line L and the depth d (distance from the surface of the detection coil of the magnetometer to the dipole) in which the dipole exists is expressed by an equation (10). The magnitude Q of the dipole is expressed by the following equation (11) when $B_0$ assumes an absolute value of a magnetic field in the peak point 804 in the positive-direction magnetic field 803 or the peak point 805 of the negative-direction magnetic field 802 where $\mu_0$ represents a vacuum magnetic permeability.

$$d = L/\sqrt{2} \tag{10}$$

$$Q = 4\pi d^2/(0.385\mu_0)B_0 \tag{11}$$

As described above, when the magnetic fields are measured by using the arrangement of the magnetometers for measuring the magnetic field component of the normal direction as shown in FIG. 22, it is possible to easily estimate the position, the direction and the magnitude of the dipole. By using the above-mentioned estimated results, it is possible to display the motion of the heart of the fetus as shown in FIG. 16.

As described above, according to the present invention, by reducing the thickness of the bottom surface of the cryostat, a signal intensity can be improved considerably and the signal intensity from the fetus can be obtained as about twice as large the conventional apparatus, thereby making it possible to improve S/N. Under generating condition in which the apparatus is in use, it is possible to effect the continuous measurement during 10 days to about two weeks. Assuming that only one dipole exists in the heart of the fetus and estimating the position of the heart obtained in accordance with the variation of the heart beat of the fetus as then the position of the dipole (current source), it becomes possible to easily monitor the movement of the heart of the fetus and the fluctuation of the heart beat. As a result, by using the small cryostat, it becomes possible to monitor electrophysiological activity of the heart of the fetus with excellent S/N.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A biomagnetic field measurement apparatus comprising:
   a plurality of magnetometers each having a SQUID sensor and a detection coil and each detecting magnetic field generated from a heart of a fetus in a pregnant woman;
   a cryostat which holds the magnetometers at a low temperature by a cooling liquid, one ends of the magnetometers being disposed on a plane parallel to a bottom surface of the cryostat:
   a processor processing magnetic field wave forms detected by the magnetometers; and
   a display displaying results obtained by the processor,
   wherein the processor estimates a position of the heart of the fetus from the magnetic field wave forms assuming one current dipole exists in the heart of the fetus, and processes projecting the position of the one current dipole on x-y plane which is the bottom surface of the cryostat and processes projecting the position of the one current dipole on y-z plane or x-z plane which is perpendicular to the x-y plane and parallel to z axis which is parallel to a center axis of the cryostat, and
   wherein the position of the one current dipole projected on the x-y plane and the position of the current dipole projected on the y-z plane or the x-z plane and a straight line representing the bottom surface of the cryostat with which the abdomen surface of the pregnant woman is closely contacted are displayed on the display, and a movement, in the x-y plane and the y-z plane or the x-z plane, of the heart of the fetus in the pregnant woman is displayed on the display.

2. A biomagnetic field measurement apparatus according to claim 1, wherein the position of the one current dipole projected on the x-y plane and the position of the current dipole projected on the y-z plane or the x-z plane are displayed at the same time in different regions on the display.

3. A biomagnetic field measurement apparatus according to claim 1, wherein positions of the one ends of the magnetometers projected on the x-y plane and the y-z plane or the x-z plane are displayed on the display.

4. A biomagnetic field measurement apparatus according to claim 1, wherein time variations on the x-y plane and the y-z plane or the x-z plane of the position of the one current dipole are displayed on the display.

5. A biomagnetic field measurement apparatus according to claim 1, wherein paths showing time variations on the x-y plane and the y-z plane or the x-z plane of the position of the one current dipole are displayed on the display.

6. A biomagnetic field measurement apparatus according to claim 1, wherein paths showing time variations on the x-y plane and the y-z plane or the x-z plane of the position of the one current dipole are displayed on the display, and the paths are displayed with a number.

7. A biomagnetic field measurement apparatus according to claim 1, wherein paths showing time variations on the x-y plane and the y-z plane or the x-z plane of the position of the one current dipole are displayed on the display, and the paths are displayed by an arrow mark.

8. A biomagnetic field measurement according to claim 1, wherein the positions on the x-y plane and the y-z plane or the x-z plane of the one current dipole are displayed on the display, and a change of a magnitude of the one current dipole is displayed by a change of a color.

9. A biomagnetic field measurement apparatus according to claim 1, wherein a moving velocity of the one current dipole is displayed on the display.

10. A biomagnetic field measurement apparatus according to claim 1, wherein a moving distance of the one current dipole is displayed on the display.

11. A biomagnetic field measurement apparatus according to claim 1, wherein an amount of rotation of the one current dipole is displayed on the display.

12. A biomagnetic field measurement apparatus according to claim 1, wherein an average velocity in the z axis direction of the one current dipole is displayed on the display.

13. A biomagnetic field measurement apparatus according to claim 1, wherein an average velocity in the x-y plane of the one current dipole is displayed on the display.

14. A biomagnetic field measurement apparatus according to claim 1, wherein a moving distance in the z axis direction of the one current dipole within a measurement time is displayed on the display.

15. A biomagnetic field measurement apparatus according to claim 1, wherein a moving distance in the x-y plane of the one current dipole within a measurement time is displayed on the display.

16. A biomagnetic field measurement apparatus according to claim 1, wherein a total amount of rotation of the one current dipole in the x-y plane is displayed on the display.

17. A biomagnetic field measurement apparatus comprising:
   a plurality of magnetometers each detecting magnetic field generated from a subject to be inspected;
   a cryostat which has a cylindrical outer surface and holds the magnetometers at a low temperature by a cooling liquid;
   a guard portion which is integrally formed with the cryostat at the cylindrical outer surface;
   a member holding the cryostat, said member having an upper plate portion which has a hole having a curvature;
   a spherical moving member which has a shape of a part of sphere and a preselected thickness, wherein the spherical part of the spherical moving member has the same curvature as that of the hole of the upper plate portion, the guard portion is fixed to an upper flat portion of the spherical moving member by a fixing screw, and the spherical part of the spherical moving member is disposed in the hole of the upper plate portion such that the spherical part of the spherical moving member can freely be rotated in the hole of the user plate portion;
   two handles, each of which is disposed on the cylindrical outer surface for setting an angle of a central axis of the cryostat in respective of two perpendicular planes; and
   two stoppers each of which is disposed at the upper plate portion and fixes the rotation of the angle of the central axis of the cryostat in respective of two perpendicular planes.

18. A biomagnetic field measurement apparatus according to claim 17 further comprising:
   two indicating lines which discriminate a rotating direction of the central axis of the cryostat and are indicated at a bottom surface of the cryostat and at the cylindrical outer surface at near the bottom surface of the cryostat.

19. A biomagnetic field measurement apparatus according to claim 18, wherein the two indicating lines are indicated by different colors, respectively.

20. A biomagnetic field measurement apparatus according to claim 17, wherein the preselected thickness of the spherical moving member is equal to or greater than a half value of the preselected thickness of the spherical moving member.

21. A biomagnetic field measurement apparatus according to claim 20, wherein a maximum inclination angle of the central axis of the cryostat is defined by $\sin^{-1}(v1/v3)=\sin^{-1}((v2/2)/v3)$, wherein v1 is a thickness of the upper plate portion, v2 is the preselected thickness of the spherical moving member and v3 is a radius of the spherical part of the spherical moving member.

22. A biomagnetic field measurement apparatus according to claim 17, wherein a thickness of the upper plate portion is equal or greater than a half value of the preselected thickness of the spherical moving member and a maximum inclination angle of the central axis of the cryostat is set within 15° to 30°.

23. A biomagnetic field measurement apparatus according to claim 17, wherein an outer diameter of the upper flat portion of the spherical moving member is substantially the same as an outer diameter of the guard portion, and an inclination angle of the central axis of the cryostat become maximum when the guard portion contacts an upper surface of the upper plate portion.

24. A biomagnetic field measurement apparatus according to claim 17, wherein the position of the one current dipole projected on the x-y plane and the position of the current dipole projected on the y-z plane or the x-z plane are displayed in different regions on the display.

25. A biomagnetic field measurement apparatus comprising:
   a plurality of magnetometers each detecting magnetic field generated from a subject to be inspected; and
   a cryostat which holds the magnetometers at a low temperature by a cooling liquid,
   wherein a member having humidity is disposed on a part of the cryostat, or a heating member is disposed on a part of the cryostat.

26. A biomagnetic field measurement apparatus comprising:
   a plurality of magnetometers each detecting magnetic field generated from a subject to be inspected; and
   a cryostat which holds the magnetometers at a low temperature by a cooling liquid,
   wherein a member for filling a gas generated from the cooling liquid in the cryostat at an upper part of the cryostat, the member is disposed at a part of the cryostat.

27. A biomagnetic field measurement apparatus comprising:
   a plurality of magnetometers each detecting magnetic field generated from a subject to be inspected;
   a cryostat which holds the magnetometers at a low temperature by a cooling liquid; and
   a member holding the cryostat,
   wherein, in the cryostat, a first tube for introducing the cooling liquid into the cryostat and a second tube which has a shape of a funnel tube at one end and into which one end of the first tube can be inserted.

28. A biomagnetic field measurement apparatus comprising:
- a plurality of magnetometers each having a SQUID sensor and a detection coil and each detecting magnetic field generated from a subject to be inspected;
- a cryostat which holds the magnetometers at a low temperature by a cooling liquid;
- a holding member which holds the cryostat such that the cryostat can be rotatable about axis of the cryostat;
- a position fitting member which has a shape same as a part of a shape including a center of a bottom surface of the cryostat and has a plurality of poles for contacting to a peripheral surface at near the bottom surface of the cryostat; and
- a weight marker which is connected to the position fitting member by string, at a position of the weight marker corresponding to the center of the bottom surface of the cryostat,
- wherein a plurality of indicating lines for discriminating a rotating direction of the cryostat are indicated at the bottom surface of the cryostat and at the peripheral surface at near the bottom surface of the cryostat, and the position fitting member is used for fitting the center of a bottom surface of the cryostat to a predetermined surface position of the subject to be inspected.

29. A biomagnetic field measurement apparatus comprising:
- a plurality of magnetometers each having a SQUID sensor and a detection coil and each detecting magnetic field generated from a heart of a fetus in a pregnant woman;
- a cryostat which holds the magnetometers at a low temperature by a cooling liquid, one ends of the magnetometers being disposed on a plane parallel to a bottom surface of the cryostat;
- a processor processing magnetic field wave forms detected by the magnetometers; and
- a display displaying results obtained by the processor,
- wherein the processor estimates a position of the heart of the foetus from the magnetic field wave forms assuming one current dipole exists in the heart of the foetus and time variations of the position of the one current dipole projected on an x-y plane which is the bottom surface of the cryostat and time variations of the position of the one current dipole projected on a y-z plane or an x-z plane which is perpendicular to the x-y plane and parallel to a z axis which is parallel to a center axis of the cryostat; and
- wherein the time variations of the position of the one current dipole projected on the x-y plane, the time variations of the position of the one current dipole projected on the y-z plane or the x-z plane and a straight line representing the bottom surface of the cryostat with which the abdomen surface of the pregnant woman is closely contacted are displayed on the display, and a movement, in the x-y plane and the y-z plane or the x-z plane, of the heart of the fetus in the pregnant woman is displayed on the display.

30. A biomagnetic field measurement apparatus according to claim 29, wherein the position of the one current dipole projected on the x-y plane and the position of the current dipole projected on the y-z plane or the x-z plane are displayed in different regions on the display.

31. A biomagnetic field measuring method comprising the steps of:
(1) detecting magnetic field generated from a heart of a fetus in a pregnant woman by a plurality of magnetometers in a cryostat filled with a cooling liquid, one ends of the magnetometers being disposed on a plane parallel to a bottom surface of the cryostat;
(2) estimating a position of the heart of the fetus from the magnetic field wave forms assuming one current dipole exists in the heart of the fetus and determining a position of the one current dipole projected on an x-y plane which is the bottom surface of the cryostat and a position of the one current dipole projected on a y-z plane or an x-z plane which is perpendicular to the x-y plane and parallel to a z axis which is parallel to a center axis of the cryostat;
(3) displaying, on a display, the position of the one current dipole projected on the x-y plane, the position of the one current dipole projected on the y-z plane or the x-z plane and a straight line representing the bottom surface of the cryostat with which the abdomen surface of the pregnant woman is closely contacted and displaying on the display a movement, in the x-y plane and the y-z plane or the x-z plane, of the heart of the fetus in the pregnant woman is displayed on the display.

32. A biomagnetic field measuring method comprising the steps of:
(1) detecting magnetic field generated from a heart of a fetus in a pregnant woman by a plurality of magnetometers in a cryostat filled with a cooling liquid, one ends of the magnetometers being disposed on a plane parallel to a bottom surface of the cryostat;
(2) estimating a position of the heart of the fetus from the magnetic field wave forms assuming one current dipole exists in the heart of the foetus and determining time variations of the position of the one current dipole projected on an x-y plane which is the bottom surface of the cryostat and time variations of the position of the one current dipole projected on a y-z plane or an x-y plane which is perpendicular to the x-y plane and parallel to a z axis which is parallel to a center axis of the cryostat;
(3) displaying, on a display, the time variations of the position of the one current dipole projected on the x-y plane, the time variations of the position of the one current dipole projected on the y-z or the x-z plane and a straight line representing the bottom surface of the cryostat with which the abdomen surface of the pregnant woman is closely contacted, and displaying on the display a movement, in the x-y plane and the y-z plane or the x-z plane, of the heart of the fetus in the pregnant woman is displayed on the display.

* * * * *